(12) United States Patent
Cines et al.

(10) Patent No.: US 7,425,534 B2
(45) Date of Patent: Sep. 16, 2008

(54) COMPOSITIONS AND METHODS FOR MODULATING MUSCLE CELL AND TISSUE CONTRACTILITY

(75) Inventors: Douglas B. Cines, Wynnewood, PA (US); Abd Al-Roof Higazi, Jerusalem (IL)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 11/019,448

(22) Filed: Dec. 21, 2004

(65) Prior Publication Data

US 2005/0158300 A1 Jul. 21, 2005

Related U.S. Application Data

(63) Continuation of application No. 09/880,503, filed on Jun. 13, 2001, now Pat. No. 6,833,357.

(60) Provisional application No. 60/212,874, filed on Jun. 20, 2000.

(51) Int. Cl.
*A61K 38/48* (2006.01)
*A61K 38/00* (2006.01)

(52) U.S. Cl. ............... 514/2; 424/94.64; 424/94.63; 424/278.1

(58) Field of Classification Search ............... 514/2; 424/94.63, 94.64; 435/217
See application file for complete search history.

(56) References Cited

U.S. PATENT DOCUMENTS

| 4,160,452 | A  |   | 7/1979  | Theeuwes        |          |
|-----------|----|---|---------|-----------------|----------|
| 4,256,108 | A  |   | 3/1981  | Theeuwes        |          |
| 4,265,874 | A  |   | 5/1981  | Bonsen et al.   |          |
| 5,292,750 | A  | * | 3/1994  | Yoshikuni et al.| 514/315  |
| 5,681,721 | A  | * | 10/1997 | Steffens et al. | 435/69.6 |
| 5,833,982 | A  | * | 11/1998 | Berkner et al.  | 424/94.64|
| 5,945,403 | A  | * | 8/1999  | Folkman et al.  | 514/21   |
| 6,497,877 | B1 | * | 12/2002 | Stringer et al. | 424/94.64|
| 6,833,357 | B2 | * | 12/2004 | Cines et al.    | 514/12   |
| 2003/0113271 | A1 | * | 6/2003 | Katyama et al.  | 424/45   |

OTHER PUBLICATIONS

Poliakov et al. (2001) Plasmin-dependent elimination of the growth-factor-like domain in urokinase causes its rapid cellular uptake and degradation. Biochem. J. 355, pp. 639-645.*
Ribatti et al. (1999) In vivo angiogenic activity of urokinase: role of endogenous fibroblast growth factor-2. J. Cell Sci. vol. 112, part 23, pp. 4213-4221.*
Koolwijk et al. (1996) Cooperative effect of TNFalpha, bFGF, and VEGF on the formation of tubular structures of human microvascular endothelial cells in a fibrin matrix. Role of urokinase activity. J. Cell Biol. vol. 132, No. 6, pp. 1177-1788.*
Bdeir et al. (2003) The kringle stabilizes urokinase binding to the urokinase receptor. Blood. vol. 102, No. 10, pp. 3600-3608.*
Mukhina et al. (2000) The chemotactic action of urokinase on smooth muscle cells is dependent on its kringle domain. Characterization of interactions and contribution to chemotaxis. J. Biol. Chem. vol. 275, No. 22, pp. 16450-16458.*
Harrington et al. (2004) Antithrombotic therapy for coronary artery disease: the Seventh ACCP Conference on Antithrombotic and Thrombolytic Therapy. Chest. vol. 126, pp. 513S-548S.*
Goto et al. (2003) Acute intracerebroventricular administration of either carboxyl-terminal or amino-terminal fragments of agouti-related peptide produces a long-term decrease in energy expenditure in rats. Int. J. Mol. Med. vol. 12, No. 3, pp. 379-383.*
NCBI Sequence Viewer 2.0 (2006) CAA01390 uPA, see http://www.ncbi.nlm.nih.gov/entrez/view.fcgi?db=protein& val=512447.*
Dumler et al. (1999) Urokinase induces activation and formation of Stat4 and Stat1-Stat2 complexes in human vascular smooth muscle cells. J. Biol. Chem. vol. 274. No. 34, pp. 24059-24065.*
START (2006) The challenge of mild asthma, http://hcp.pulmicort.com/article /502140.aspx, p. 1.*
Franco et al. (2006) Activation of urokinase receptor by a novel interaction between the connecting peptide region of urokinase and alpha v beta 5 integrin. J. Cell Sci., vol. 119, part 16, pp. 3424-3434.*
Winn et al. (2005) The role of endothelial cell apoptosis in inflammatory and immune diseases. J. Thromb. Haemost. vol. 3, No. 8, pp. 1815-1824.*
Altschul et al., 1990, J. Mol. Biol. 215:403-410.
Altschul et al., 1997, Nucleic Acids Res. 25:3389-3402.
Bacharach et al., 1992, Proc. Natl. Acad. Sci. USA 89:10686-10690.
Bugge et al., 1996, Proc. Natl. Acad. Sci USA 93:5899-5904.
Carmeliet et al., 1994, Nature 368:419-424.
Carmeliet et al., 1996, Haemostasis 26:132-153.
Carmeliet et al., 1997, Cir. res. 81:829-839.
Carmeliet et al., 1998, J. Cell Biol. 140:233-245.
Chang et al., 1992, Br. J. Pharmacol. 107:983-989.
Clowes et al., 1990, Circ. Res. 67:61-67.
Degryse et al., 1999, Blood 94:649-662.

(Continued)

*Primary Examiner*—Karen Cocrhane Carlson
*Assistant Examiner*—Samuel Wei Liu
(74) *Attorney, Agent, or Firm*—Drinker Biddle & Reath LLP

(57) ABSTRACT

The present invention relates to compositions and methods comprising one or more domains of urokinase-type plasminogen activator (uPA) in an amount effective to modulate one or more of the contractility and angiogenic activity of a mammalian muscle or endothelial cell or tissue for use in the treatment of a disease or condition having as a symptom thereof one or more of abnormal muscle cell or tissue contractility and abnormal angiogenic activity. The one or more domains of uPA can be present in the inventive compositions and methods either as part of the full uPA molecule in either single chain or two chain form (scuPA or tcuPA), or as an isolated polypeptide, or a fragment of the uPA molecule (e.g., the amino terminal fragment "ATF"), or a deletion mutant of the uPA molecule. The inventive methods comprise administering to a mammal afflicted with such a disease or condition the inventive composition, and modulating one or more of the contractility and the angiogenic activity of the muscle or endothelial cell or tissue, thereby treating the disease or condition. Kits for treating such diseases are also included.

1 Claim, 14 Drawing Sheets

OTHER PUBLICATIONS

DePetro et al., 1994, Exp. Cell Res. 213:286-294.
Goldberg et al., eds, 1997, In: Regulation of Angiogenesis, Birkhauser Verlag, Basel, pp. 391-411.
Gurewich et al., 1987, Semin. Thromb. Hemost. 13:146-151.
Higazi et al., 1995, J. Biol. Chem. 270:17375-17380.
Higazi et al., 1996, Biochemistry 35:6884-6890.
Higazi et al., 1996, Thromb. Res. 84:243-251.
Higazi et al., 1998, Blood 92:2075-2083.
Husain, 1991, Biochemistry 30:5797-5805.
Johnsson et al., 1995, J. Mol. Recognit. 8:125-131.
Kanse et al., 1997, Arteriosclerosis, Thromb., and Vas. Biol. 17:2848-2854.
Karlin et al., 1990, Proc. Natl. Acad. Sci. USA 87:2264-2268.
Karlin et al., 1993, Proc. Natl. Acad. Sci. USA 90:5873-5877.
Kirchheimer et al., 1987, Fed. Am. Soc. of Exper. Biol. and Med. Journal 1:125-128.
Koopman et al., 1998, J. Biol. Chem. 273:33267-33272.
Linjen et al., 1998, Arterioscler. Thromb. Vasc. Biol. 18:1035-1045.
Noda-Heiny et al., 1995, Arterioscler. Thromb. Vasc. Biol. 15:37-43.
Odekon et al., 1992, J. Cell. Physiol. 150:258-263.
Oyama et al., 1986, Eur. J. Pharmacol. 131:75-78.
Pedersen et al., 1996, Br. J. Haematol. 95:45-51.
Pepper et al., 1990, J. Cell. Biol. 111:743-755.
Pinsky et al., 1998, J. Clin. Invest. 102:919-928.
Rabbani et al., 1992, J. Biol. Chem. 267:14151-14156.
Shireman et al., 1997, J. Vasc. Surg. 25:157-164.
Urano et al., 1988, Arch. Biochem. Biophys. 264:222-230.

* cited by examiner

FIG 1A.
KTCYEGNGHFYRGKASTDTMGRPCLPWNSATVLQQTYHAHRSDALQLGL
GKHNYCRNPDNRRRPWCYVQVGLKPLVQECMVHDCADGK

FIG 1B.
SNELHQVPSNCDCLNGGTCVSNKYFSNIHWCNCPKKFGGQHCEIDKS

FIG 1C.
SNELHQVPSNCDCLNGGTCVSNKYFSNIHWCNCPKKFGGQHCEIDKSKTC
YEGNGHFYRGKASTDTMGRPCLPWNSATVLQQTYHAHRSDALQLGLGK
HNYCRNPDNRRRPWCYVQVGLKPLVQECMVHDCADGKKPSSPPEELKFQ
CGQKTLRPRFKIIGGEFTTIENQPWFAAIYRRHRGGSVTYVCGGSLISPCWV
ISATHCFIDYPKKEDYIVYLGRSRLNSNTQGEMKFEVENLILHKDYSADTL
AHHNDIALLKIRSKEGRCAQPSRTIQTICLPSMYNDPQFGTSCEITGFGKENS
TDYLYPEQLKMTVVKLISHRECQQPHYYGSEVTTKMLCAADPQWKTDSC
QGDSGGPLVCSLQGRMTLTGIVSWGRGCALKDKPGVYTRVSHFLPWIRSH
TKEENGLAL

FIG 1D.
SNELHQVPSNCDCLNGGTCVSNKYFSNIHWCNCPKKFGGQHCEIDKSKTC
YEGNGHFYRGKASTDTMGRPCLPWNSATVLQQTYHAHRSDALQLGLGK
HNYCRNPDNRRRPWCYVQVGLKPLVQECMVHDCADGK

FIG 1E.
KPSSPPEELKFQCGQKTLRPRFKIIGGEFTTIENQPWFAAIYRRHRGGSVTY
VCGGSLISPCWVISATHCFIDYPKKEDYIVYLGRSRLNSNTQGEMKFEVEN
LILHKDYSADTLAHHNDIALLKIRSKEGRCAQPSRTIQTICLPSMYNDPQFG
TSCEITGFGKENSTDYLYPEQLKMTVVKLISHRECQQPHYYGSEVTTKMLC
AADPQWKTDSCQGDSGGPLVCSLQGRMTLTGIVSWGRGCALKDKPGVYT
RVSHFLPWIRSHTKEENGLAL

FIG 1F.

SNELHQVPSNCDCLNGGTCVSNKYFSNIHWCNCPKKFGGQHCEIDKSKTC
YEGNGHFYRGKASTDTMGRPCLPWNSATVLQQTYHAHRSDALQLGLGK
HNYCRNPDNRRRPWCYVQVGLKPLVQECMVHDCADGK//LKFQCGQKTL
RPRFKIIGGEFTTIENQPWFAAIYRRHRGGSVTYVCGGSLISPCWVISATHCF
IDYPKKEDYIVYLGRSRLNSNTQGEMKFEVENLILHKDYSADTLAHHNDIA
LLKIRSKEGRCAQPSRTIQTICLPSMYNDPQFGTSCEITGFGKENSTDYLYPE
QLKMTVVKLISHRECQQPHYYGSEVTTKMLCAADPQWKTDSCQGDSGGP
LVCSLQGRMTLTGIVSWGRGCALKDKPGVYTRVSHFLPWIRSHTKEENGL
AL

FIG 1G.

SNELHQVPSNCDCLNGGTCVSNKYFSNIHWCNCPKKFGGQHCEIDKS//KPS
SPPEELKFQCGQKTLRPRFKIIGGEFTTIENQPWFAAIYRRHRGGSVTYVCG
GSLISPCWVISATHCFIDYPKKEDYIVYLGRSRLNSNTQGEMKFEVENLILH
KDYSADTLAHHNDIALLKIRSKEGRCAQPSRTIQTICLPSMYNDPQFGTSCE
ITGFGKENSTDYLYPEQLKMTVVKLISHRECQQPHYYGSEVTTKMLCAAD
PQWKTDSCQGDSGGPLVCSLQGRMTLTGIVSWGRGCALKDKPGVYTRVS
HFLPWIRSHTKEENGLAL

FIG 1H.

SNELHQVPSNCDCLNGGTCVSNKYFSNIHWCNCPKKFGGQHCEIDKSKTC
YEGNGHFYRGKASTDTMGRPCLPWNSATVLQQTYHAHRSDALQLGLGK
HNYCRNPDNRRRPWCYVQVGLKPLVQECMVHDCADGKKPSSPPEE

FIG 1I.

KTCYEGNGHFYRGKASTDTMGRPCLPWNSATVLQQTYHAHRSDALQLGL
GKHNYCRNPDNRRRPWCYVOVGLKPLVQECMVHDCADGKKPSSPPEE

FIG 1J.

aaaacctgctatgaggggaatggtcacttttaccgaggaaaggccagcactgaca
ccatgggccggccctgcctgccctggaactctgccactgtccttcagcaaacgta
ccatgcccacagatctgatgctcttcagctgggcctggggaaacataattactgc
aggaacccagacaaccggaggcgaccctggtgctatgtgcaggtgggcctaaagc
cgcttgtccaagagtgcatggtgcatgactgcgcagatggaaaa

FIG 1K.

agcaatgaacttcatcaagttccatcgaactgtgactgtctaaatggaggaacat
gtgtgtccaacaagtacttctccaacattcactggtgcaactgcccaaagaatt
cggagggcagcactgtgaaatagataagtca

FIG 1L.

agcaatgaacttcatcaagttccatcgaactgtgactgtctaaatggaggaacat
gtgtgtccaacaagtacttctccaacattcactggtgcaactgcccaaagaatt
cggagggcagcactgtgaaatagataagtcaaaaacctgctatgaggggaatggt
cacttttaccgaggaaaggccagcactgacaccatgggccggccctgcctgccct
ggaactctgccactgtccttcagcaaacgtaccatgcccacagatctgatgctct
tcagctgggcctggggaaacataattactgcaggaacccagacaaccggaggcga
ccctggtgctatgtgcaggtgggcctaaagccgcttgtccaagagtgcatggtgc
atgactgcgcagatggaaaaaagccctcctcctccagaagaattaaaatttca
gtgtggccaaaagactctgaggccccgctttaagattattgggggagaattcacc
accatcgagaaccagccctggtttgcggccatctacaggaggcaccgggggggct
ctgtcacctacgtgtgtggaggcagcctcatcagcccttgctgggtgatcagcgc
cacacactgcttcattgattacccaaagaaggaggactacatcgtctacctgggt
cgctcaaggcttaactccaacacgcaaggggagatgaagtttgaggtggaaaacc
tcatcctacacaaggactacagcgctgacacgcttgctcaccacaacgacattgc
cttgctgaagatccgttccaaggagggcaggtgtgcgcagccatcccggactata
cagaccatctgcctgccctcgatgtataacgatccccagtttggcacaagctgtg
agatcactggctttggaaaagagaattctaccgactatctctatccggagcagct
gaaaatgactgttgtgaagctgatttcccaccgggagtgtcagcagcccactac
tacggctctgaagtcaccaccaaaatgctatgtgctgctgaccccaatggaaaa
cagattcctgccagggagactcaggggacccctcgtctgttccctccaaggccg
catgactttgactggaattgtgagctggggccgtggatgtgccctgaaggacaag
ccaggcgtctacacgagagtctcacacttcttaccctggatccgcagtcacacca
aggaagagaatggcctggccctctga

FIG 1M.

agcaatgaacttcatcaagttccatcgaactgtgactgtctaaatggaggaacat
gtgtgtccaacaagtacttctccaacattcactggtgcaactgcccaaagaaatt
cggagggcagcactgtgaaatagataagtcaaaaacctgctatgaggggaatggt
cacttttaccgaggaaaggccagcactgacaccatgggccggccctgcctgccct
ggaactctgccactgtccttcagcaaacgtaccatgcccacagatctgatgctct
tcagctgggcctggggaaacataattactgcaggaacccagacaaccggaggcga
ccctggtgctatgtgcaggtgggcctaaagccgcttgtccaagagtgcatggtgc
atgactgcgcagatggaaaa

FIG 1N.

aagccctcctctcctccagaagaattaaaatttcagtgtggccaaaagactctga
ggccccgctttaagattattgggggagaattcaccaccatcgagaaccagccctg
gtttgcggccatctacaggaggcaccggggggctctgtcacctacgtgtgtgga
ggcagcctcatcagccttgctgggtgatcagcgccacacactgcttcattgatt
acccaaagaaggaggactacatcgtctacctgggtcgctcaaggcttaactccaa
cacgcaaggggagatgaagtttgaggtggaaacctcatcctacacaaggactac
agcgctgacacgcttgctcaccacaacgacattgcttgctgaagatccgttcca
aggagggcaggtgtgcgcagccatcccggactatacagaccatctgcctgccctc
gatgtataacgatcccagtttggcacaagctgtgagatcactggctttggaaaa
gagaattctaccgactatctctatccggagcagctgaaaatgactgttgtgaagc
tgatttcccaccgggagtgtcagcagcccactactacggctctgaagtcaccac
caaaatgctatgtgctgctgaccccaatggaaaacagattcctgccagggagac
tcaggggggaccgtcgtctgttccctccaaggccgcatgactttgactggaattg
tgagctggggccgtggatgtgccctgaaggacaagccaggcgtctacacgagagt
ctcacacttcttaccctggatccgcagtcacaccaaggaagagaatggcctggcc
ctctga

FIG 10.

agcaatgaacttcatcaagttccatcgaactgtgactgtctaaatggaggaacat
gtgtgtccaacaagtacttctccaacattcactggtgcaactgcccaaagaaatt
cggagggcagcactgtgaaatagataagtcaaaaacctgctatgagggaatggt
cacttttaccgaggaaaggccagcactgacaccatgggccggccctgcctgccct
ggaactctgccactgtccttcagcaaacgtaccatgcccacagatctgatgctct
tcagctgggcctggggaaacataattactgcaggaacccagacaaccggaggcga
ccctggtgctatgtgcaggtgggcctaaagccgcttgtccaagagtgcatggtgc
atgactgcgcagatggaaaattaaaatttcagtgtggccaaaagactctgaggcc
ccgctttaagattattgggggagaattcaccaccatcgagaaccagccctggttt
gcggccatctacaggaggcaccggggggctctgtcacctacgtgtgtggaggca
gcctcatcagcccttgctgggtgatcagcgccacacactgcttcattgattaccc
aaagaaggaggactacatcgtctacctgggtcgctcaaggcttaactccaacacg
caaggggagatgaagtttgaggtggaaaacctcatcctacacaaggactacagcg
ctgacacgcttgctcaccacaacgacattgccttgctgaagatccgttccaagga
gggcaggtgtgcgcagccatcccggactatacagaccatctgcctgccctcgatg
tataacgatccccagtttggcacaagctgtgagatcactggctttggaaaagaga
attctaccgactatctctatccggagcagctgaaaatgactgttgtgaagctgat
ttcccaccgggagtgtcagcagcccactactacggctctgaagtcaccaccaaa
atgctatgtgctgctgaccccaatggaaaacagattcctgccagggagactcag
ggggacccctcgtctgttcctccaaggccgcatgactttgactggaattgtgag
ctggggccgtggatgtgccctgaaggacaagccaggcgtctacacgagagtctca
cacttcttaccctggatccgcagtcacaccaaggaagagaatggcctggccctct
ga

FIG 1P.

agcaatgaacttcatcaagttccatcgaactgtgactgtctaaatggaggaacat
gtgtgtccaacaagtacttctccaacattcactggtgcaactgcccaaagaaatt
cggagggcagcactgtgaaatagataagtcaaagccctcctctcctccagaagaa
ttaaaatttcagtgtggccaaaagactctgaggccccgctttaagattattgggg
gagaattcaccaccatcgagaaccagccctggtttgcggccatctacaggaggca
ccggggggggctctgtcacctacgtgtgtggaggcagcctcatcagccttgctgg
gtgatcagcgccacacactgcttcattgattacccaaagaaggaggactacatcg
tctacctgggtcgctcaaggcttaactccaacacgcaaggggagatgaagtttga
ggtggaaaacctcatcctacacaaggactacagcgctgacacgcttgctcaccac
aacgacattgccttgctgaagatccgttccaaggagggcaggtgtgcgcagccat
cccggactatacagaccatctgcctgccctcgatgtataacgatcccagtttgg
cacaagctgtgagatcactggctttggaaaagagaattctaccgactatctctat
ccggagcagctgaaaatgactgttgtgaagctgatttcccaccgggagtgtcagc
agccccactactacggctctgaagtcaccaccaaaatgctatgtgctgctgaccc
ccaatggaaaacagattcctgccagggagactcaggggggaccccctcgtctgttcc
ctccaaggccgcatgactttgactggaattgtgagctggggccgtggatgtgccc
tgaaggacaagccaggcgtctacacgagagtctcacacttcttaccctggatccg
cagtcacaccaaggaagagaatggcctggccctctga

FIG 1Q.

agcaatgaacttcatcaagttccatcgaactgtgactgtctaaatggaggaacat
gtgtgtccaacaagtacttctccaacattcactggtgcaactgcccaaagaaatt
cggagggcagcactgtgaaatagataagtcaaaacctgctatgagggggaatggt
cacttttaccgaggaaaggccagcactgacaccatgggccggccctgcctgccct
ggaactctgccactgtccttcagcaaacgtaccatgcccacagatctgatgctct
tcagctgggcctggggaaacataattactgcaggaacccagacaaccggaggcga
ccctggtgctatgtgcaggtgggcctaaagccgcttgtccaagagtgcatggtgc
atgactgcgcagatggaaaaaagccctcctcctccagaagaa

FIG 1R.

aaaacctgctatgaggggaatggtcacttttaccgaggaaaggccagcactgaca
ccatgggccggccctgcctgccctggaactctgccactgtccttcagcaaacgta
ccatgcccacagatctgatgctcttcagctgggcctggggaaacataattactgc
aggaacccagacaaccggaggcgaccctggtgctatgtgcaggtgggcctaaagc
cgcttgtccaagagtgcatggtgcatgactgcgcagatggaaaaaagccctcctc
tcctccagaagaa A
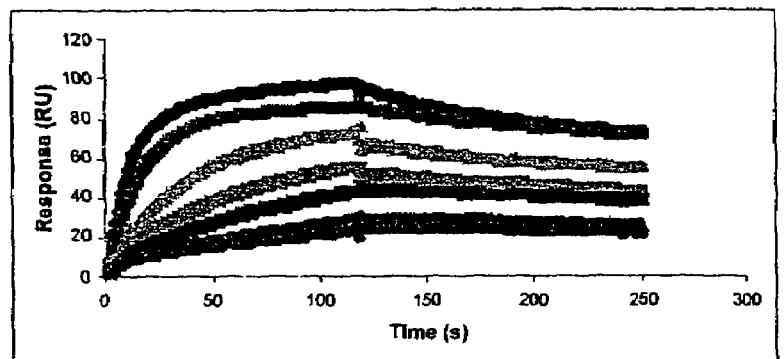
B
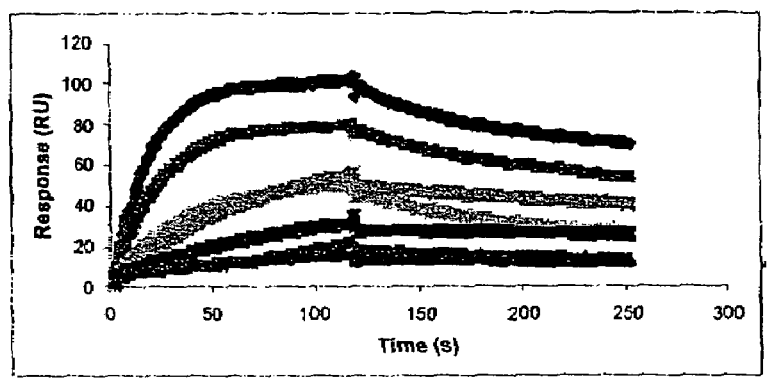
C
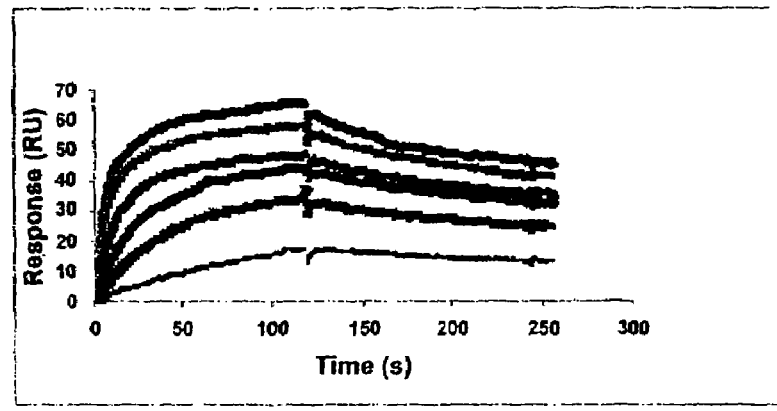
FIGURE 6

SEQUENCE LISTING

```
<160> NUMBER OF SEQ ID NOS: 18

<210> SEQ ID NO 1
<211> LENGTH: 88
<212> TYPE: PRT
<213> ORGANISM: Homo sapiens

<400> SEQUENCE: 1

Lys Thr Cys Tyr Glu Gly Asn Gly His Phe Tyr Arg Gly Lys Ala Ser
1               5                   10                  15

Thr Asp Thr Met Gly Arg Pro Cys Leu Pro Trp Asn Ser Ala Thr Val
            20                  25                  30

Leu Gln Gln Thr Tyr His Ala His Arg Ser Asp Ala Leu Gln Leu Gly
        35                  40                  45

Leu Gly Lys His Asn Tyr Cys Arg Asn Pro Asp Asn Arg Arg Arg Pro
    50                  55                  60
```

```
Trp Cys Tyr Val Gln Val Gly Leu Lys Pro Leu Val Gln Glu Cys Met
 65                  70                  75                  80

Val His Asp Cys Ala Asp Gly Lys
                 85

<210> SEQ ID NO 2
<211> LENGTH: 47
<212> TYPE: PRT
<213> ORGANISM: Homo sapiens

<400> SEQUENCE: 2

Ser Asn Glu Leu His Gln Val Pro Ser Asn Cys Asp Cys Leu Asn Gly
  1               5                  10                  15

Gly Thr Cys Val Ser Asn Lys Tyr Phe Ser Asn Ile His Trp Cys Asn
                 20                  25                  30

Cys Pro Lys Lys Phe Gly Gly Gln His Cys Glu Ile Asp Lys Ser
             35                  40                  45

<210> SEQ ID NO 3
<211> LENGTH: 411
<212> TYPE: PRT
<213> ORGANISM: Homo sapiens

<400> SEQUENCE: 3

Ser Asn Glu Leu His Gln Val Pro Ser Asn Cys Asp Cys Leu Asn Gly
  1               5                  10                  15

Gly Thr Cys Val Ser Asn Lys Tyr Phe Ser Asn Ile His Trp Cys Asn
                 20                  25                  30

Cys Pro Lys Lys Phe Gly Gly Gln His Cys Glu Ile Asp Lys Ser Lys
             35                  40                  45

Thr Cys Tyr Glu Gly Asn Gly His Phe Tyr Arg Gly Lys Ala Ser Thr
 50                  55                  60

Asp Thr Met Gly Arg Pro Cys Leu Pro Trp Asn Ser Ala Thr Val Leu
 65                  70                  75                  80

Gln Gln Thr Tyr His Ala His Arg Ser Asp Ala Leu Gln Leu Gly Leu
                 85                  90                  95

Gly Lys His Asn Tyr Cys Arg Asn Pro Asp Asn Arg Arg Arg Pro Trp
            100                 105                 110

Cys Tyr Val Gln Val Gly Leu Lys Pro Leu Val Gln Glu Cys Met Val
            115                 120                 125

His Asp Cys Ala Asp Gly Lys Lys Pro Ser Ser Pro Glu Glu Leu
130                 135                 140

Lys Phe Gln Cys Gly Gln Lys Thr Leu Arg Pro Arg Phe Lys Ile Ile
145                 150                 155                 160

Gly Gly Glu Phe Thr Thr Ile Glu Asn Gln Pro Trp Phe Ala Ala Ile
                165                 170                 175

Tyr Arg Arg His Arg Gly Gly Ser Val Thr Tyr Val Cys Gly Gly Ser
                180                 185                 190

Leu Ile Ser Pro Cys Trp Val Ile Ser Ala Thr His Cys Phe Ile Asp
            195                 200                 205

Tyr Pro Lys Lys Glu Asp Tyr Ile Val Tyr Leu Gly Arg Ser Arg Leu
210                 215                 220

Asn Ser Asn Thr Gln Gly Glu Met Lys Phe Glu Val Glu Asn Leu Ile
225                 230                 235                 240

Leu His Lys Asp Tyr Ser Ala Asp Thr Leu Ala His His Asn Asp Ile
                245                 250                 255
```

```
Ala Leu Leu Lys Ile Arg Ser Lys Glu Gly Arg Cys Ala Gln Pro Ser
            260                 265                 270

Arg Thr Ile Gln Thr Ile Cys Leu Pro Ser Met Tyr Asn Asp Pro Gln
        275                 280                 285

Phe Gly Thr Ser Cys Glu Ile Thr Gly Phe Gly Lys Glu Asn Ser Thr
    290                 295                 300

Asp Tyr Leu Tyr Pro Glu Gln Leu Lys Met Thr Val Lys Leu Ile
305                 310                 315                 320

Ser His Arg Glu Cys Gln Gln Pro His Tyr Tyr Gly Ser Glu Val Thr
                325                 330                 335

Thr Lys Met Leu Cys Ala Ala Asp Pro Gln Trp Lys Thr Asp Ser Cys
            340                 345                 350

Gln Gly Asp Ser Gly Gly Pro Leu Val Cys Ser Leu Gln Gly Arg Met
        355                 360                 365

Thr Leu Thr Gly Ile Val Ser Trp Gly Arg Gly Cys Ala Leu Lys Asp
    370                 375                 380

Lys Pro Gly Val Tyr Thr Arg Val Ser His Phe Leu Pro Trp Ile Arg
385                 390                 395                 400

Ser His Thr Lys Glu Glu Asn Gly Leu Ala Leu
                405                 410

<210> SEQ ID NO 4
<211> LENGTH: 135
<212> TYPE: PRT
<213> ORGANISM: Homo sapiens

<400> SEQUENCE: 4

Ser Asn Glu Leu His Gln Val Pro Ser Asn Cys Asp Cys Leu Asn Gly
1               5                   10                  15

Gly Thr Cys Val Ser Asn Lys Tyr Phe Ser Asn Ile His Trp Cys Asn
            20                  25                  30

Cys Pro Lys Lys Phe Gly Gly Gln His Cys Glu Ile Asp Lys Ser Lys
        35                  40                  45

Thr Cys Tyr Glu Gly Asn Gly His Phe Tyr Arg Gly Lys Ala Ser Thr
    50                  55                  60

Asp Thr Met Gly Arg Pro Cys Leu Pro Trp Asn Ser Ala Thr Val Leu
65                  70                  75                  80

Gln Gln Thr Tyr His Ala His Arg Ser Asp Ala Leu Gln Leu Gly Leu
                85                  90                  95

Gly Lys His Asn Tyr Cys Arg Asn Pro Asp Asn Arg Arg Arg Pro Trp
            100                 105                 110

Cys Tyr Val Gln Val Gly Leu Lys Pro Leu Val Gln Glu Cys Met Val
        115                 120                 125

His Asp Cys Ala Asp Gly Lys
    130                 135

<210> SEQ ID NO 5
<211> LENGTH: 276
<212> TYPE: PRT
<213> ORGANISM: Homo sapiens

<400> SEQUENCE: 5

Lys Pro Ser Ser Pro Pro Glu Glu Leu Lys Phe Gln Cys Gly Gln Lys
1               5                   10                  15

Thr Leu Arg Pro Arg Phe Lys Ile Ile Gly Gly Glu Phe Thr Thr Ile
            20                  25                  30
```

```
Glu Asn Gln Pro Trp Phe Ala Ala Ile Tyr Arg Arg His Arg Gly Gly
            35                  40                  45

Ser Val Thr Tyr Val Cys Gly Gly Ser Leu Ile Ser Pro Cys Trp Val
 50                  55                  60

Ile Ser Ala Thr His Cys Phe Ile Asp Tyr Pro Lys Lys Glu Asp Tyr
 65                  70                  75                  80

Ile Val Tyr Leu Gly Arg Ser Arg Leu Asn Ser Asn Thr Gln Gly Glu
                 85                  90                  95

Met Lys Phe Glu Val Glu Asn Leu Ile Leu His Lys Asp Tyr Ser Ala
            100                 105                 110

Asp Thr Leu Ala His His Asn Asp Ile Ala Leu Leu Lys Ile Arg Ser
            115                 120                 125

Lys Glu Gly Arg Cys Ala Gln Pro Ser Arg Thr Ile Gln Thr Ile Cys
130                 135                 140

Leu Pro Ser Met Tyr Asn Asp Pro Gln Phe Gly Thr Ser Cys Glu Ile
145                 150                 155                 160

Thr Gly Phe Gly Lys Glu Asn Ser Thr Asp Tyr Leu Tyr Pro Glu Gln
                165                 170                 175

Leu Lys Met Thr Val Val Lys Leu Ile Ser His Arg Glu Cys Gln Gln
            180                 185                 190

Pro His Tyr Tyr Gly Ser Glu Val Thr Thr Lys Met Leu Cys Ala Ala
            195                 200                 205

Asp Pro Gln Trp Lys Thr Asp Ser Cys Gln Gly Asp Ser Gly Gly Pro
210                 215                 220

Leu Val Cys Ser Leu Gln Gly Arg Met Thr Leu Thr Gly Ile Val Ser
225                 230                 235                 240

Trp Gly Arg Gly Cys Ala Leu Lys Asp Lys Pro Gly Val Tyr Thr Arg
                245                 250                 255

Val Ser His Phe Leu Pro Trp Ile Arg Ser His Thr Lys Glu Glu Asn
            260                 265                 270

Gly Leu Ala Leu
            275

<210> SEQ ID NO 6
<211> LENGTH: 403
<212> TYPE: PRT
<213> ORGANISM: Homo sapiens

<400> SEQUENCE: 6

Ser Asn Glu Leu His Gln Val Pro Ser Asn Cys Asp Cys Leu Asn Gly
 1               5                  10                  15

Gly Thr Cys Val Ser Asn Lys Tyr Phe Ser Asn Ile His Trp Cys Asn
                20                  25                  30

Cys Pro Lys Lys Phe Gly Gly Gln His Cys Glu Ile Asp Lys Ser Lys
            35                  40                  45

Thr Cys Tyr Glu Gly Asn Gly His Phe Tyr Arg Gly Lys Ala Ser Thr
 50                  55                  60

Asp Thr Met Gly Arg Pro Cys Leu Pro Trp Asn Ser Ala Thr Val Leu
 65                  70                  75                  80

Gln Gln Thr Tyr His Ala His Arg Ser Asp Ala Leu Gln Leu Gly Leu
                 85                  90                  95

Gly Lys His Asn Tyr Cys Arg Asn Pro Asp Asn Arg Arg Arg Pro Trp
            100                 105                 110

Cys Tyr Val Gln Val Gly Leu Lys Pro Leu Val Gln Glu Cys Met Val
            115                 120                 125
```

-continued

```
His Asp Cys Ala Asp Gly Lys Leu Lys Phe Gln Cys Gly Gln Lys Thr
    130                 135                 140
Leu Arg Pro Arg Phe Lys Ile Ile Gly Gly Glu Phe Thr Thr Ile Glu
145                 150                 155                 160
Asn Gln Pro Trp Phe Ala Ala Ile Tyr Arg Arg His Arg Gly Gly Ser
                165                 170                 175
Val Thr Tyr Val Cys Gly Gly Ser Leu Ile Ser Pro Cys Trp Val Ile
            180                 185                 190
Ser Ala Thr His Cys Phe Ile Asp Tyr Pro Lys Lys Glu Asp Tyr Ile
        195                 200                 205
Val Tyr Leu Gly Arg Ser Arg Leu Asn Ser Asn Thr Gln Gly Glu Met
    210                 215                 220
Lys Phe Glu Val Glu Asn Leu Ile Leu His Lys Asp Tyr Ser Ala Asp
225                 230                 235                 240
Thr Leu Ala His His Asn Asp Ile Ala Leu Leu Lys Ile Arg Ser Lys
                245                 250                 255
Glu Gly Arg Cys Ala Gln Pro Ser Arg Thr Ile Gln Thr Ile Cys Leu
            260                 265                 270
Pro Ser Met Tyr Asn Asp Pro Gln Phe Gly Thr Ser Cys Glu Ile Thr
        275                 280                 285
Gly Phe Gly Lys Glu Asn Ser Thr Asp Tyr Leu Tyr Pro Glu Gln Leu
    290                 295                 300
Lys Met Thr Val Val Lys Leu Ile Ser His Arg Glu Cys Gln Gln Pro
305                 310                 315                 320
His Tyr Tyr Gly Ser Glu Val Thr Thr Lys Met Leu Cys Ala Ala Asp
                325                 330                 335
Pro Gln Trp Lys Thr Asp Ser Cys Gln Gly Asp Ser Gly Gly Pro Leu
            340                 345                 350
Val Cys Ser Leu Gln Gly Arg Met Thr Leu Thr Gly Ile Val Ser Trp
        355                 360                 365
Gly Arg Gly Cys Ala Leu Lys Asp Lys Pro Gly Val Tyr Thr Arg Val
    370                 375                 380
Ser His Phe Leu Pro Trp Ile Arg Ser His Thr Lys Glu Glu Asn Gly
385                 390                 395                 400
Leu Ala Leu

<210> SEQ ID NO 7
<211> LENGTH: 323
<212> TYPE: PRT
<213> ORGANISM: Homo sapiens

<400> SEQUENCE: 7

Ser Asn Glu Leu His Gln Val Pro Ser Asn Cys Asp Cys Leu Asn Gly
1               5                   10                  15
Gly Thr Cys Val Ser Asn Lys Tyr Phe Ser Asn Ile His Trp Cys Asn
            20                  25                  30
Cys Pro Lys Lys Phe Gly Gly Gln His Cys Glu Ile Asp Lys Ser Lys
        35                  40                  45
Pro Ser Ser Pro Pro Glu Glu Leu Lys Phe Gln Cys Gly Gln Lys Thr
    50                  55                  60
Leu Arg Pro Arg Phe Lys Ile Ile Gly Gly Glu Phe Thr Thr Ile Glu
65                  70                  75                  80
Asn Gln Pro Trp Phe Ala Ala Ile Tyr Arg Arg His Arg Gly Gly Ser
                85                  90                  95
```

Val Thr Tyr Val Cys Gly Gly Ser Leu Ile Ser Pro Cys Trp Val Ile
            100                 105                 110

Ser Ala Thr His Cys Phe Ile Asp Tyr Pro Lys Lys Glu Asp Tyr Ile
            115                 120                 125

Val Tyr Leu Gly Arg Ser Arg Leu Asn Ser Asn Thr Gln Gly Glu Met
            130                 135                 140

Lys Phe Glu Val Glu Asn Leu Ile Leu His Lys Asp Tyr Ser Ala Asp
145                 150                 155                 160

Thr Leu Ala His His Asn Asp Ile Ala Leu Leu Lys Ile Arg Ser Lys
                165                 170                 175

Glu Gly Arg Cys Ala Gln Pro Ser Arg Thr Ile Gln Thr Ile Cys Leu
            180                 185                 190

Pro Ser Met Tyr Asn Asp Pro Gln Phe Gly Thr Ser Cys Glu Ile Thr
            195                 200                 205

Gly Phe Gly Lys Glu Asn Ser Thr Asp Tyr Leu Tyr Pro Glu Gln Leu
            210                 215                 220

Lys Met Thr Val Val Lys Leu Ile Ser His Arg Glu Cys Gln Gln Pro
225                 230                 235                 240

His Tyr Tyr Gly Ser Glu Val Thr Thr Lys Met Leu Cys Ala Ala Asp
                245                 250                 255

Pro Gln Trp Lys Thr Asp Ser Cys Gln Gly Asp Ser Gly Gly Pro Leu
            260                 265                 270

Val Cys Ser Leu Gln Gly Arg Met Thr Leu Thr Gly Ile Val Ser Trp
            275                 280                 285

Gly Arg Gly Cys Ala Leu Lys Asp Lys Pro Gly Val Tyr Thr Arg Val
            290                 295                 300

Ser His Phe Leu Pro Trp Ile Arg Ser His Thr Lys Glu Glu Asn Gly
305                 310                 315                 320

Leu Ala Leu

<210> SEQ ID NO 8
<211> LENGTH: 143
<212> TYPE: PRT
<213> ORGANISM: Homo sapiens

<400> SEQUENCE: 8

Ser Asn Glu Leu His Gln Val Pro Ser Asn Cys Asp Cys Leu Asn Gly
1               5                   10                  15

Gly Thr Cys Val Ser Asn Lys Tyr Phe Ser Asn Ile His Trp Cys Asn
            20                  25                  30

Cys Pro Lys Lys Phe Gly Gly Gln His Cys Glu Ile Asp Lys Ser Lys
            35                  40                  45

Thr Cys Tyr Glu Gly Asn Gly His Phe Tyr Arg Gly Lys Ala Ser Thr
        50                  55                  60

Asp Thr Met Gly Arg Pro Cys Leu Pro Trp Asn Ser Ala Thr Val Leu
65                  70                  75                  80

Gln Gln Thr Tyr His Ala His Arg Ser Asp Ala Leu Gln Leu Gly Leu
                85                  90                  95

Gly Lys His Asn Tyr Cys Arg Asn Pro Asp Asn Arg Arg Arg Pro Trp
            100                 105                 110

Cys Tyr Val Gln Val Gly Leu Lys Pro Leu Val Gln Glu Cys Met Val
            115                 120                 125

His Asp Cys Ala Asp Gly Lys Lys Pro Ser Ser Pro Pro Glu Glu
            130                 135                 140

<210> SEQ ID NO 9
<211> LENGTH: 96
<212> TYPE: PRT
<213> ORGANISM: Homo sapiens

<400> SEQUENCE: 9

```
Lys Thr Cys Tyr Glu Gly Asn Gly His Phe Tyr Arg Gly Lys Ala Ser
1               5                   10                  15

Thr Asp Thr Met Gly Arg Pro Cys Leu Pro Trp Asn Ser Ala Thr Val
            20                  25                  30

Leu Gln Gln Thr Tyr His Ala His Arg Ser Asp Ala Leu Gln Leu Gly
        35                  40                  45

Leu Gly Lys His Asn Tyr Cys Arg Asn Pro Asp Asn Arg Arg Arg Pro
    50                  55                  60

Trp Cys Tyr Val Gln Val Gly Leu Lys Pro Leu Val Gln Glu Cys Met
65                  70                  75                  80

Val His Asp Cys Ala Asp Gly Lys Lys Pro Ser Ser Pro Pro Glu Glu
                85                  90                  95
```

<210> SEQ ID NO 10
<211> LENGTH: 264
<212> TYPE: DNA
<213> ORGANISM: Homo sapiens

<400> SEQUENCE: 10

```
aaaacctgct atgaggggaa tggtcacttt taccgaggaa aggccagcac tgacaccatg    60
ggccggccct gcctgccctg gaactctgcc actgtccttc agcaaacgta ccatgcccac   120
agatctgatg ctcttcagct gggcctgggg aaacataatt actgcaggaa cccagacaac   180
cggaggcgac cctggtgcta tgtgcaggtg ggcctaaagc cgcttgtcca agagtgcatg   240
gtgcatgact gcgcagatgg aaaa                                          264
```

<210> SEQ ID NO 11
<211> LENGTH: 141
<212> TYPE: DNA
<213> ORGANISM: Homo sapiens

<400> SEQUENCE: 11

```
agcaatgaac ttcatcaagt tccatcgaac tgtgactgtc taaatggagg aacatgtgtg    60
tccaacaagt acttctccaa cattcactgg tgcaactgcc aaagaaatt cggagggcag   120 cactgtgaaa tagataagtc a                                             141
```

<210> SEQ ID NO 12
<211> LENGTH: 1236
<212> TYPE: DNA
<213> ORGANISM: Homo sapiens

<400> SEQUENCE: 12

```
agcaatgaac ttcatcaagt tccatcgaac tgtgactgtc taaatggagg aacatgtgtg    60
tccaacaagt acttctccaa cattcactgg tgcaactgcc aaagaaatt cggagggcag   120 cactgtgaaa tagataagtc aaaaacctgc tatgaggggga atggtcactt ttaccgagga   180
aaggccagca ctgacaccat gggccggccc tgcctgccct ggaactctgc cactgtcctt   240
cagcaaacgt accatgccca cagatctgat gctcttcagc tgggcctggg gaaacataat   300
tactgcagga acccagacaa ccggaggcga ccctggtgct atgtgcaggt gggcctaaag   360
```

-continued

```
ccgcttgtcc aagagtgcat ggtgcatgac tgcgcagatg gaaaaaagcc ctcctctcct      420
ccagaagaat taaaatttca gtgtggccaa aagactctga ggccccgctt taagattatt      480
gggggagaat tcaccaccat cgagaaccag ccctggtttg cggccatcta caggaggcac      540
cgggggggct ctgtcaccta cgtgtgtgga ggcagcctca tcagcccttg ctgggtgatc      600
agcgccacac actgcttcat tgattaccca aagaaggagg actacatcgt ctacctgggt      660
cgctcaaggc ttaactccaa cacgcaaggg gagatgaagt tgaggtgga aaacctcatc      720 ctacacaagg actacagcgc tgacacgctt gctcaccaca cgacattgc cttgctgaag      780 atccgttcca aggagggcag gtgtgcgcag ccatcccgga ctatacagac catctgcctg      840
ccctcgatgt ataacgatcc ccagtttggc acaagctgtg agatcactgg ctttggaaaa      900
gagaattcta ccgactatct ctatccggag cagctgaaaa tgactgttgt gaagctgatt      960
tcccaccggg agtgtcagca gccccactac tacggctctg aagtcaccac caaaatgcta     1020
tgtgctgctg accccaatg aaaacagat tcctgccagg gagactcagg ggacccctc     1080 gtctgttccc tccaaggccg catgactttg actggaattg tgagctgggg ccgtggatgt     1140
gccctgaagg acaagccagg cgtctacacg agagtctcac acttcttacc ctggatccgc     1200
agtcacacca aggaagagaa tggcctggcc ctctga                                1236

<210> SEQ ID NO 13
<211> LENGTH: 405
<212> TYPE: DNA
<213> ORGANISM: Homo sapiens

<400> SEQUENCE: 13
agcaatgaac ttcatcaagt tccatcgaac tgtgactgtc taaatggagg aacatgtgtg       60
tccaacaagt acttctccaa cattcactgg tgcaactgcc caagaaaatt cggagggcag      120
cactgtgaaa tagataagtc aaaaacctgc tatgagggga atggtcactt ttaccgagga      180
aaggccagca ctgacaccat gggccggccc tgcctgccct ggaactctgc cactgtcctt      240
cagcaaacgt accatgccca cagatctgat gctcttcagc tgggcctggg gaaacataat      300
tactgcagga acccagacaa ccggaggcga ccctggtgct atgtgcaggt gggcctaaag      360
ccgcttgtcc aagagtgcat ggtgcatgac tgcgcagatg gaaaa                      405

<210> SEQ ID NO 14
<211> LENGTH: 831
<212> TYPE: DNA
<213> ORGANISM: Homo sapiens

<400> SEQUENCE: 14
aagccctcct ctcctccaga agaattaaaa tttcagtgtg gccaaaagac tctgaggccc       60
cgctttaaga ttattggggg agaattcacc accatcgaga accagccctg gtttgcggcc      120
atctacagga ggcaccgggg gggctctgtc acctacgtgt gtggaggcag cctcatcagc      180
ccttgctggg tgatcagcgc cacacactgc ttcattgatt acccaaagaa ggaggactac      240
atcgtctacc tgggtcgctc aaggcttaac tccaacacgc aagggagat gaagtttgag      300 gtggaaaacc tcatcctaca caaggactac agcgctgaca cgcttgctca ccacaacgac      360
attgccttgc tgaagatccg ttccaaggag ggcaggtgtg cgcagccatc ccggactata      420
cagaccatct gcctgccctc gatgtataac gatccccagt ttggcacaag ctgtgagatc      480
actggctttg gaaagagaa ttctaccgac tatctctatc cggagcagct gaaaatgact      540
gttgtgaagc tgatttccca ccgggagtgt cagcagcccc actactacgg ctctgaagtc      600
```

| | |
|---|---|
| accaccaaaa tgctatgtgc tgctgacccc caatggaaaa cagattcctg ccagggagac | 660 |
| tcaggggggac ccctcgtctg ttccctccaa ggccgcatga ctttgactgg aattgtgagc | 720 |
| tggggccgtg gatgtgccct gaaggacaag ccaggcgtct acacgagagt ctcacacttc | 780 |
| ttaccctgga tccgcagtca caccaaggaa gagaatggcc tggccctctg a | 831 |

<210> SEQ ID NO 15
<211> LENGTH: 1212
<212> TYPE: DNA
<213> ORGANISM: Homo sapiens

<400> SEQUENCE: 15

| | |
|---|---|
| agcaatgaac ttcatcaagt tccatcgaac tgtgactgtc taaatggagg aacatgtgtg | 60 |
| tccaacaagt acttctccaa cattcactgg tgcaactgcc caagaaaatt cggagggcag | 120 |
| cactgtgaaa tagataagtc aaaaacctgc tatgagggga atggtcactt ttaccgagga | 180 |
| aaggccagca ctgacaccat gggccggccc tgcctgccct ggaactctgc cactgtcctt | 240 |
| cagcaaacgt accatgccca cagatctgat gctcttcagc tgggcctggg gaaacataat | 300 |
| tactgcagga acccagacaa ccggaggcga ccctggtgct atgtgcaggt gggcctaaag | 360 |
| ccgcttgtcc aagagtgcat ggtgcatgac tgcgcagatg gaaaattaaa atttcagtgt | 420 |
| ggccaaaaga ctctgaggcc ccgctttaag attattgggg gagaattcac caccatcgag | 480 |
| aaccagcccct ggtttgcggc catctacagg aggcaccggg ggggctctgt cacctacgtg | 540 |
| tgtggaggca gcctcatcag cccttgctgg gtgatcagcg ccacacactg cttcattgat | 600 |
| tacccaaaga aggaggacta catcgtctac ctgggtcgct caaggcttaa ctccaacacg | 660 |
| caaggggaga tgaagtttga ggtggaaaac ctcatcctac acaaggacta cagcgctgac | 720 |
| acgcttgctc accacaacga cattgccttg ctgaagatcc gttccaagga gggcaggtgt | 780 |
| gcgcagccat cccggactat acagaccatc tgcctgccct cgatgtataa cgatccccag | 840 |
| tttggcacaa gctgtgagat cactggcttt ggaaaagaga attctaccga ctatctctat | 900 |
| ccggagcagc tgaaaatgac tgttgtgaag ctgatttccc accggagtg tcagcagccc | 960 |
| cactactacg gctctgaagt caccaccaaa atgctatgtg ctgctgaccc ccaatggaaa | 1020 |
| acagattcct gccagggaga ctcagggggga cccctcgtct gttccctcca aggccgcatg | 1080 |
| actttgactg gaattgtgag ctggggccgt ggatgtgccc tgaaggacaa gccaggcgtc | 1140 |
| tacacgagag tctcacactt cttaccctgg atccgcagtc acaccaagga agagaatggc | 1200 |
| ctggccctct ga | 1212 |

<210> SEQ ID NO 16
<211> LENGTH: 972
<212> TYPE: DNA
<213> ORGANISM: Homo sapiens

<400> SEQUENCE: 16

| | |
|---|---|
| agcaatgaac ttcatcaagt tccatcgaac tgtgactgtc taaatggagg aacatgtgtg | 60 |
| tccaacaagt acttctccaa cattcactgg tgcaactgcc caagaaaatt cggagggcag | 120 |
| cactgtgaaa tagataagtc aaagccctcc tctcctccag aagaattaaa atttcagtgt | 180 |
| ggccaaaaga ctctgaggcc ccgctttaag attattgggg gagaattcac caccatcgag | 240 |
| aaccagcccct ggtttgcggc catctacagg aggcaccggg ggggctctgt cacctacgtg | 300 |
| tgtggaggca gcctcatcag cccttgctgg gtgatcagcg ccacacactg cttcattgat | 360 |

```
                                                   -continued
tacccaaaga aggaggacta catcgtctac ctgggtcgct caaggcttaa ctccaacacg      420 caagggaga tgaagtttga ggtggaaaac ctcatcctac acaaggacta cagcgctgac       480
acgcttgctc accacaacga cattgccttg ctgaagatcc gttccaagga gggcaggtgt      540
gcgcagccat cccggactat acagaccatc tgcctgccct cgatgtataa cgatccccag     600
tttggcacaa gctgtgagat cactggcttt ggaaaagaga attctaccga ctatctctat     660
ccggagcagc tgaaaatgac tgttgtgaag ctgatttccc accgggagtg tcagcagccc    720
cactactacg gctctgaagt caccaccaaa atgctatgtg ctgctgaccc ccaatggaaa     780
acagattcct gccagggaga ctcagggga cccctcgtct gttccctcca aggccgcatg     840
actttgactg gaattgtgag ctggggccgt ggatgtgccc tgaaggacaa gccaggcgtc    900
tacacgagag tctcacactt cttaccctgg atccgcagtc acaccaagga agagaatggc    960
ctggccctct ga                                                         972

<210> SEQ ID NO 17
<211> LENGTH: 429
<212> TYPE: DNA
<213> ORGANISM: Homo sapiens

<400> SEQUENCE: 17
agcaatgaac ttcatcaagt tccatcgaac tgtgactgtc taaatggagg aacatgtgtg      60
tccaacaagt acttctccaa cattcactgg tgcaactgcc caagaaatt cggagggcag      120 cactgtgaaa tagataagtc aaaaacctgc tatgagggga atggtcactt ttaccgagga     180
aaggccagca ctgacaccat gggccggccc tgcctgccct ggaactctgc cactgtcctt     240
cagcaaacgt accatgccca cagatctgat gctcttcagc tgggcctggg gaaacataat    300
tactgcagga acccagacaa ccggaggcga ccctggtgct atgtgcaggt gggcctaaag     360
ccgcttgtcc aagagtgcat ggtgcatgac tgcgcagatg gaaaaaagcc ctcctctcct    420
ccagaagaa                                                             429

<210> SEQ ID NO 18
<211> LENGTH: 288
<212> TYPE: DNA
<213> ORGANISM: Homo sapiens

<400> SEQUENCE: 18
aaaacctgct atgagggaa tggtcacttt taccgaggaa aggccagcac tgacaccatg       60
ggccggccct gcctgccctg gaactctgcc actgtccttc agcaaacgta ccatgcccac    120
agatctgatg ctcttcagct gggcctgggg aaacataatt actgcaggaa cccagacaac    180
cggaggcgac cctggtgcta tgtgcaggtg ggcctaaagc cgcttgtcca agagtgcatg    240
gtgcatgact gcgcagatgg aaaaaagccc tcctctcctc agaagaa                  288
```

US 7,425,534 B2

COMPOSITIONS AND METHODS FOR MODULATING MUSCLE CELL AND TISSUE CONTRACTILITY

CROSS REFERENCE TO RELATED APPLICATIONS

The present application is a continuation of U.S. application Ser. No. 09/880,503, filed on Jun. 13, 2001, now issued as U.S. Pat. No. 6,833,357, which claims priority to U.S. Provisional Patent Application No. 60/212,874, filed on Jun. 20, 2000, all of which are incorporated by reference herein in their entirety.

STATEMENT REGARDING FEDERALLY SUPPORTED RESEARCH AND DEVELOPMENT

This invention was supported in part by U.S. Government finds (NIH Grant No. HL 60169), and the U.S. Government may therefore have certain rights in the invention.

BACKGROUND OF THE INVENTION

Urokinase-type plasminogen activator (uPA) is a serine protease which has been implicated in various biological processes, including fibrinolysis, (Carmeliet et al., 1994, Nature 369:419-424; Carmeliet et al., 1996, Haemostasis 26:132-153; Pinsky et al., 1998, J. Clin. Invest. 102:919-928; Bugge et al., 1996, Proc. Natl. Acad. Sci. USA 93:5899-5904) angiogenesis, (Odekon et al., 1992, J. Cell, Physiol. 150:258-263; Bacharach et al., 1992, Proc. Natl. Acad. Sci. USA 89:10686; Pepper et al., 1990, J. Cell Biol. 111:743-755; Goldberg et al., eds., 1997, In: Regulation of Angiogenesis Birkhauser Verlag, Basel, pp. 391-411) neointima and aneurysm formation, (Clowes et al., 1990, Circ. Res. 67:61-67; Carmeliet et al., 1997, Circ. Res. 81:829-839; Shireman et al., 1997, J. Vasc. Surg. 25:157-164; Noda-Heiny et al., 1995, Arterioscler. Thromb. Vasc. Biol. 15:37-43; Lijnen et al., 1998, Arterioscler. Thromb. Vasc. Biol. 18:1035-1045) chemotaxis, (Pedersen et al., 1996, Br. J. Haematol. 95:45-51) and wound healing (Carmeliet et al., 1998, J. Cell Biol. 140:233-245).

Certain of these activities may require the proteolytic activity of uPA, (Kirschheimer et al., 1987, Fed. Am. Soc. of Exper. Biol. and Med. Journal 1:125-128; DePetro et al., 1994, Exp. Cell Res. 213:186-194) whereas others involve intracellular signaling through the urokinase receptor (uPAR) (Pedersen et al., 1996, Br. J. Haematol. 95:45-51; Degryse et al., 1999, Blood 94:649-662) or additional, as yet undefined receptors (Carmeliet et al., 1998, J. Cell Biol. 140:233-245; Kanse et al., 1997, Arteriosclerosis, Thromb., and Vas. Biol. 17:2848-2854; Koopman et al., 1998, J. Biol. Chem. 273: 33267-33272; Rabbani et al., 1992, J. Biol. Chem. 267: 14151-14156).

Urokinase is synthesized as a single chain molecule (scuPA) which exhibits little or no intrinsic enzymatic activity (Urano et al., 1988, Arch. Biochem. Biophys. 264:222-230; Gurewich et al., 1987, Semin. Thromb. Hemost. 13:146-151; Husain, 1991, Biochemistry 30:5707-5805). scuPA is a multi-domain protein composed of a C-terminal protease domain and an amino-terminal fragment (ATF). The ATF is composed of two domains: a growth factor domain (GFD) which binds to uPAR, and a kringle domain (uPA kringle), the function of which has heretofore been unknown. scuPA can be cleaved by plasmin at the $Lys^{158}$-$Ile^{159}$ position to generate an enzymatically active, disulfide-linked two-chain urokinase molecule (tcuPA). Between the ATF and the protease domain is a region designated the connecting peptide (corresponding to amino acids 136-158).

It is hypothesized that the natural enzyme uPA is normally used in the human body to dissolve clots and to facilitate cell migration. Although uPA is known in the art as a useful therapeutic molecule for the treatment of diseases and disorders having as a symptom thereof abnormal clotting in critical blood vessels, there remains a need in the art for compositions and methods which are useful for the treatment of such diseases as well as for the treatment of diseases and disorders having as symptoms abnormally high or abnormally low muscle cell contractility or undesirable angiogenic activity. Such diseases and conditions include the following: cardiovascular diseases and conditions such as hypotension, hypertension and atherosclerosis; thrombotic conditions such as stroke, heart attack and post angioplasty stenting; angiogenic disorders; respiratory diseases and conditions such as pulmonary fibrosis and asthma; diseases and disorders related to tumor cell invasion, angiogenesis and metastasis; wound healing and clotting disorders and reproductive disorders such as premature uterine contraction and impotence. The present invention meets these needs.

BRIEF SUMMARY OF THE INVENTION

The invention includes a composition comprising the urokinase-type plasminogen activator (uPA) kringle in an amount effective to modulate one or more of the contractility and the angiogenic activity of a mammalian muscle or endothelial cell or tissue. The uPA kringle shares at least about 75% homology with a polypeptide having the amino acid sequence corresponding to SEQ ID NO:1.

In one embodiment, the composition further comprises one or more domains of uPA selected from the group consisting of the growth factor domain, the connecting peptide and the protease domain.

The invention also includes a composition comprising the growth factor domain of uPA in an amount effective to modulate the contractility of a mammalian muscle cell or tissue. The growth factor domain shares at least about 75% homology with a polypeptide having the amino acid sequence corresponding to SEQ ID NO:2.

In one embodiment, the composition further comprises one or more domains of uPA selected from the group consisting of the uPA kringle, the connecting peptide and the protease domain.

The invention also includes a composition comprising a polypeptide, the polypeptide (LMW-uPA) comprising the connecting peptide and protease domains of uPA in an amount effective to inhibit the contractility of a mammalian muscle cell or tissue. The polypeptide shares at least about 75% homology with a polypeptide having the amino acid sequence corresponding to SEQ ID NO:5.

In one aspect, the cell is in a mammal.

In another aspect, the muscle cell is selected from the group consisting of a smooth muscle cell, a striated muscle cell and a cardiac muscle cell, and the muscle tissue is selected from the group consisting of a smooth muscle tissue, a striated muscle tissue and a cardiac muscle tissue.

In one embodiment, the composition further comprises an inducing compound in an amount effective to mediate the contraction of a mammalian muscle cell or tissue. The inducing compound is selected from the group consisting of phenylepherine, epinepherine, acetylcholine and endothelin.

In another aspect, the composition comprises two chain urokinase (tcuPA). The tcuPA shares at least about 75% homology with a polypeptide having the amino acid sequence corresponding to SEQ ID NO:3.

In one embodiment, the composition comprises single chain urokinase (scuPA). The scuPA shares at least about 75% homology with a polypeptide having the amino acid sequence corresponding to SEQ ID NO:3.

In another embodiment, the composition comprises the amino terminal fragment (ATF) of uPA. The ATF shares at least about 75% homology with a polypeptide having the amino acid sequence corresponding to SEQ ID NO:4.

In one aspect, the uPA kringle is an isolated kringle.

In another aspect, the growth factor domain is an isolated growth factor domain.

In yet another aspect, the ATF is an isolated ATF.

In one embodiment, modulating the contractility of the muscle cell or tissue comprises enhancing or disinhibiting the contractility of the muscle cell or tissue.

In another embodiment, modulating the contractility of the muscle cell or tissue comprises enhancing or disinhibiting the contractility of the muscle cell or tissue.

In one aspect, the cell or tissue is a vascular smooth muscle or endothelial cell or tissue, and the uPA kringle is present in an amount effective to modulate the angiogenic activity of the cell or tissue.

In another aspect, the cell or tissue is a vascular smooth muscle cell or tissue or a vascular endothelial cell or tissue.

In one embodiment, modulating the contractility of the muscle cell or tissue comprises inhibiting the contractility of the muscle cell or tissue.

In another embodiment, modulating the contractility of the muscle cell or tissue comprises inhibiting the contractility of the muscle cell or tissue.

In one aspect, the cell or tissue is a bronchial smooth muscle cell or tissue.

In one embodiment, the composition comprises the deletion mutant polypeptide scuPA$^{\Delta 136-143}$ in an amount effective to enhance or disinhibit the contractility of a mammalian muscle cell or tissue, wherein the scuPA$^{\Delta 136-143}$ shares at least about 75% homology with a polypeptide having the amino acid sequence corresponding to SEQ ID NO:6.

In another embodiment, the composition comprises a deletion mutant polypeptide selected from the group consisting of Δkringle-scuPA and Δkringle-tcuPA in an amount effective to proteolytically activate plasminogen and to inhibit the contractility of a mammalian muscle cell or tissue, wherein the Δkringle-scuPA and the Δkingle-tcuPA each share at least about 75% homology with a polypeptide having the amino acid sequence corresponding to SEQ ID NO:7.

In a further embodiment, the composition comprises a polypeptide, the polypeptide comprising the amino terminal fragment (ATF) and the connecting peptide of uPA, wherein the polypeptide shares at least about 75% homology with a polypeptide having the amino acid sequence corresponding to SEQ ID NO:8.

In yet a further embodiment, the composition comprises a polypeptide, the polypeptide comprising the uPA kringle and the connecting peptide, wherein the polypeptide shares at least about 75% homology with a polypeptide having the amino acid sequence corresponding to SEQ ID NO:9.

In one aspect, the composition is in the form of a pharmaceutical composition.

The invention also includes a composition comprising one or more polypeptides, each of the polypeptides having an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8 and SEQ ID NO:9. The one or more polypeptides are present in an amount effective to modulate one or more of the contractility and the angiogenic activity of a mammalian muscle or endothelial cell or tissue.

The invention also includes a composition comprising an isolated nucleic acid. The isolated nucleic acid has a nucleotide sequence which shares at least about 75% homology with a nucleotide sequence selected from the group consisting of SEQ ID NO:10, SEQ ID NO:11, SEQ ID NO:12, SEQ ID NO:13, SEQ ID NO:14, SEQ ID NO:15, SEQ ID NO:16, SEQ ID NO:17 and SEQ ID NO:18. The isolated nucleic acid is present in the composition in an amount effective to transform a mammalian muscle or endothelial cell to provide transgene expression of a polypeptide at a level of expression effective to modulate one or more of the contractility and angiogenic activity of the muscle or endothelial cell after transfection with the isolated nucleic acid.

The invention includes a method of treating a mammal afflicted with a disease or condition having as a symptom thereof one or more of abnormal muscle cell or tissue contractility and abnormal muscle or endothelial cell or tissue angiogenic activity. The method comprises a) administering to the mammal a composition comprising the uPA kringle in an amount effective to modulate one or more of the contractility and the angiogenic activity of a mammalian muscle or endothelial cell or tissue, wherein the uPA kringle shares at least about 75% homology with a polypeptide having the amino acid sequence corresponding to SEQ ID NO:1; and b) modulating one or more of the contractility and the angiogenic activity of the muscle or endothelial cell or tissue having one or more of abnormal contractility and abnormal angiogenic activity, whereby the disease or condition in the mammal is treated.

In one embodiment, the uPA kringle is a part of a polypeptide which shares at least about 75% homology with a polypeptide selected from the group consisting of SEQ ID NO:3 (tcuPA), SEQ ID NO:4 (ATF), SEQ ID NO:6 (scuPA$^{\Delta 136-143}$), SEQ ID NO:8 and SEQ ID NO:9.

In one aspect, the composition further comprises one or more of an agonist of the uPA kringle, an agonist of a binding protein of the uPA kringle, an antagonist of the uPA growth factor domain, an antagonist of the connecting peptide, an antagonist of a binding protein of the uPA growth factor domain, and an antagonist of a binding protein of the connecting peptide.

In another aspect, the disease or condition is selected from the group consisting of hypotension, hypertension, atherosclerosis, stroke, heart attack, microvascular occlusions, thrombotic microangiopathies, surgically induced thrombotic disorders, angiogenic disorders, pulmonary fibrosis, asthma, tumor cell invasion, tumor cell angiogenesis, tumor cell metastasis, glaucoma diabetic retinopathy, a wound healing or clotting disorder, a uterine contraction disorder and male impotence.

The invention also includes a method for treating a mammal afflicted with a disease or condition having as a symptom thereof one or more of abnormal muscle cell or tissue contractility and abnormal muscle or endothelial cell or tissue angiogenic activity. The method comprises a) administering to the mammal a composition comprising the uPA growth factor domain in an amount effective to modulate one or more of the contractility and the angiogenic activity of a mammalian muscle or endothelial cell or tissue, wherein the uPA growth factor domain shares at least about 75% homology with a polypeptide having the amino acid sequence corresponding to SEQ ID NO:2; and b) modulating one or more of the contractility and the angiogenic activity of the muscle or endothelial cell or tissue having one or more of abnormal contractility and abnormal angiogenic activity, whereby the disease or condition in the mammal is treated.

In one aspect, the composition comprises the uPA growth factor domain as part of a polypeptide which shares at least about 75% homology with a polypeptide having the amino acid sequence selected from the group consisting of SEQ ID NO:3 (scuPA), SEQ ID NO:4 (ATF), SEQ ID NO:6 (scuPA$^{\Delta 136-143}$), SEQ ID NO:7 (Δkringle-scuPA or Δkringle-tcuPA) and SEQ ID NO:8.

In one embodiment, the composition further comprises one or more of an agonist of the uPA growth factor domain, an agonist of the connecting peptide, an agonist of a binding protein of the growth factor domain, an agonist of a binding protein of the connecting peptide, an antagonist of the uPA kringle, and an antagonist of a binding protein of the uPA kringle.

In one aspect, the composition is administered to the mammal in an amount effective to inhibit the contractility of a mammalian smooth muscle cell or tissue.

In another aspect, the smooth muscle cell or tissue is a vascular smooth muscle cell or tissue, and the disease or condition treated is hypertension.

In another embodiment, the disease or condition is a respiratory disease or condition selected from the group consisting of asthma, adult respiratory distress syndrome, primary pulmonary hypertension, microvascular thrombotic occlusion and a disorder associated with chronic intrapulmonary fibrin formation.

In one aspect, the uPA kringle is present in an amount effective to inhibit the contractility of a bronchial smooth muscle cell or tissue and is a part of a polypeptide selected from the group consisting of an isolated kringle, ATF, tcuPA, scuPA$^{\Delta 136-143}$ SEQ ID NO:8 and SEQ ID NO:9.

In one embodiment, the disease or condition in the mammal sought to be treated has as a symptom thereof abnormally low vascular smooth muscle cell or tissue contractility.

In another aspect, the uPA kringle is present in an amount effective to enhance or disinhibit the contractility of a vascular smooth muscle cell or tissue and is a part of a polypeptide selected from the group consisting of an isolated kringle, ATF, tcuPA, scuPA$^{\Delta 136-143}$, SEQ ID NO:8 and SEQ ID NO:9.

In one embodiment, the disease or condition has as a symptom thereof abnormally high vascular smooth muscle cell or tissue contractility.

In one aspect, the uPA growth factor domain is present in the composition in an amount effective to inhibit the contractility of a vascular smooth muscle cell or tissue, and is present in the composition as a part of a polypeptide selected from the group consisting of an isolated growth factor domain, scuPA, Δkringle-scuPA and Δkringle-tcuPA.

The invention also includes a method of identifying a compound which is an agonist or antagonist of one or more of the uPA kringle or a binding protein thereof, the uPA growth factor domain or a binding protein thereof, and the connecting peptide or a binding protein thereof, upon the contractility or angiogenic activity of a mammalian muscle or endothelial cell or tissue. The method comprises a) providing to a first cell and an otherwise identical second cell a composition comprising a polypeptide, the polypeptide comprising one or more of the uPA kringle, the uPA growth factor domain and the connecting peptide, wherein the polypeptide is present in the composition in an amount effective to modulate the contractility or angiogenic activity of a mammalian muscle or endothelial cell or tissue; b) providing to the first cell a test compound; c) assessing the contractility or the angiogenic activity of the first cell and the second cell prior to and after administering the composition and the test compound to the first cell, and prior to and after administering the composition to the second cell; and d) comparing the contractility or angiogenic activity of the first cell with the contractility or angiogenic activity of the second cell prior to and after administration of the composition and the test compound. When the effect of the composition upon contractility or angiogenic activity in the first cell is either increased or decreased relative to the effect of the composition upon contractility or angiogenic activity in the second cell, a compound is identified which is an agonist or antagonist of one or more of the uPA kringle or a binding protein thereof, the uPA growth factor domain or a binding protein thereof, and the connecting peptide or a binding protein thereof, upon the contractility or angiogenic activity of a mammalian muscle or endothelial cell or tissue.

The invention also includes a method of treating a disease or condition in a mammal having as a symptom thereof one or more of abnormal muscle cell or tissue contractility and abnormal angiogenic activity. The method comprises a) administering to the mammal an amount suspected to be effective for modulating the contractility or angiogenic activity of a mammalian muscle or endothelial cell or tissue of an agonist or antagonist of one or more of the uPA kringle or a binding protein thereof, the uPA growth factor domain or a binding protein thereof, and the connecting peptide or a binding protein thereof; b) providing the agonist or antagonist to a muscle or endothelial cell or tissue in the mammal having abnormal contractility or abnormal angiogenic activity, or to a tissue or fluid which is contiguous therewith; and c) modulating the effect of one or more of the uPA kringle or a binding protein thereof, the uPA growth factor domain or a binding protein thereof, and the connecting peptide or a binding protein thereof, upon the muscle or endothelial cell or tissue having abnormal contractility or abnormal angiogenic activity, whereby a disease or condition in the mammal having abnormal muscle cell or tissue contractility or abnormal angiogenic activity as a symptom thereof is treated.

In one embodiment, the disease or condition treated is the vascular disease hypertension.

In another embodiment, the agonist or antagonist is one or more of an antagonist to the uPA kringle, an antagonist to a binding protein of the uPA kringle, an agonist of the uPA growth factor domain, an agonist of a binding protein of the UPA growth factor domain, an agonist of the connecting peptide, and an agonist of a binding protein of the connecting peptide.

In one aspect, the disease or condition treated is selected from the group consisting of asthma, adult respiratory distress syndrome, primary pulmonary hypertension, microvascular thrombotic occlusion and a disorder associated with chronic intrapulmonary fibrin formation.

In another aspect, the agonist or antagonist is one or more of an agonist to the uPA kringle and an agonist to a binding protein of the uPA kringle.

The invention also includes a method of identifying whether a test protein is a binding protein of one or more of the uPA kringle, the uPA growth factor domain and the connecting peptide. The method comprises a) assessing the contractility modulating effect or the angiogenic activity modulating effect of one or more of the uPA kringle, the uPA growth factor receptor and the connecting peptide upon a first cell or tissue, wherein the first cell or tissue comprises the test protein or is contiguous with a tissue or fluid of a mammal which comprises the test protein; b) assessing the contractility modulating effect or the angiogenic activity modulating effect of one or more of the uPA kringle, the uPA growth factor receptor and the connecting peptide upon a second, otherwise identical cell or tissue which does not comprise the test protein and which is not contiguous with a tissue or fluid which comprises the test protein; and c) comparing the contractility modulating effect or the angiogenic activity modulating effect in the first cell or tissue with the contractility modulating effect or the angiogenic activity modulating effect in the second cell or tissue. If the contractility modulating effect or the angiogenic activity modulating effect of one or more of the uPA kringle, the uPA growth factor receptor and the connecting peptide is greater in the first cell or tissue relative to the second cell or tissue, then the test protein is a binding protein of one or more of the uPA kringle, the uPA growth factor receptor and the connecting peptide.

Also included in the invention is a method of identifying a functional element of one or more of the uPA kringle, the uPA growth factor domain and the connecting peptide, the functional element participating in the modulation of contractility or angiogenic activity of a mammalian muscle or endothelial cell or tissue. The method comprises a) preparing one or more mutant polypeptides which lack a portion of the amino acid sequence of one or more of the uPA kringle, the uPA growth factor domain and the connecting peptide; b) assessing the ability of each of the mutant polypeptides to modulate the contractility or angiogenic activity of a mammalian muscle or endothelial cell or tissue once provided to the cell or tissue, or to a tissue or fluid which is contiguous with the cell or tissue; c) identifying, from b) a mutant polypeptide which is not able to modulate the contractility or angiogenic activity of a mammalian muscle or endothelial cell or tissue; and d) determining from c) and a) the corresponding deleted portion of the amino acid sequence of one or more of the uPA kringle, the uPA growth factor domain and the connecting peptide which participates in the modulation of muscle or endothelial cell or tissue contractility or angiogenic activity, whereby a functional element of one or more of the uPA kringle, the uPA growth factor domain and the connecting peptide is identified.

The invention also includes a method of treating a vascular disease or condition in a mammal having as a symptom thereof abnormally high fibrin clot formation. The method comprises a) administering to the mammal a composition comprising one or more of Δkringle-scuPA, Δkringle-tcuPA, an antagonist of the uPA kringle and an antagonist of a binding protein of the uPA kringle in an amount effective to inhibit the contractility of a mammalian vascular smooth muscle cell or tissue, wherein the Δkringle-scuPA and Δkringle-tcuPA share at least about 75% homology with the polypeptide corresponding to SEQ ID NO:7; b) providing the composition to an affected vascular smooth muscle cell or tissue of the cardiovascular system of the mammal which has or is prone to excessive fibrin clot formation, or to a tissue or fluid which is contiguous therewith; and c) vasodilating the affected vascular smooth muscle cell or tissue by inhibiting the contractility of the affected vascular smooth muscle cell or tissue, thereby promoting both fibrin clot lysis and vasodilation in the affected area of the vasculature of the mammal, thereby treating the vascular disease or condition.

The invention also includes a kit for treating a disease or condition in a mammal, the disease or condition having as a symptom thereof one or more of abnormal muscle cell or tissue contractility and abnormal angiogenic activity. The kit comprises a) a composition comprising a polypeptide, the polypeptide comprising one or more of the uPA kringle, the uPA growth factor domain, and the connecting peptide in an amount effective to modulate one or more of the contractility and the angiogenic activity of a mammalian muscle or endothelial cell or tissue; and b) an instructional material.

In one aspect, the kit further comprises a sterile solvent suitable for dissolving or suspending the composition prior to administering the composition to the mammal.

BRIEF DESCRIPTION OF THE DRAWINGS

The foregoing summary, as well as the following detailed description of the invention, will be better understood when read in conjunction with the appended drawings.

FIG. 1, comprising FIGS. 1A-1R, is a listing of the amino acid and nucleotide sequences SEQ ID NOs:1-18. FIG. 1A is the amino acid sequence of the uPA kringle (SEQ ID NO:1). FIG. 1B is the amino acid sequence of the uPA growth factor domain (SEQ ID NO:2). FIG. 1C is the amino acid sequence of scuPA and tcuPA (SEQ ID NO:3). FIG. 1D is the amino acid sequence of ATF (SEQ ID NO:4). FIG. 1E is the amino acid sequence of LMW-uPA (SEQ ID NO:5). FIG. 1F is the amino acid sequence of scuPA$^{\Delta 136-143}$ (SEQ ID NO:6). FIG. 1G is the amino acid sequence of Δkringle-scuPA and Δkringle-tcuPA (SEQ ID NO:7). FIG. 1H is the amino acid sequence of ATF+the connecting peptide (SEQ ID NO:8). FIG. 1I is the amino acid sequence of the uPA kringle+the connecting peptide (SEQ ID NO:9). FIG. 1J is the nucleotide sequence SEQ ID NO:10. FIG. 1K is the nucleotide sequence SEQ ID NO:11. FIG. 1L is the nucleotide sequence SEQ ID NO:12. FIG. 1M is the nucleotide sequence SEQ ID NO:13. FIG. 1N is the nucleotide sequence SEQ ID NO:14. FIG. 1O is the nucleotide sequence SEQ ID NO:15. FIG. 1P is the nucleotide sequence SEQ ID NO:16. FIG. 1Q is the nucleotide sequence SEQ ID NO:17. FIG. 1R is the nucleotide sequence SEQ ID NO:18.

FIG. 5, comprising FIG. 5A depicts the results after aortic rings were incubated with 10 nM tcuPA$^{\Delta 136-143}$ (■), 10 nM scuPA$^{\Delta 136-143}$ (▲) or PBS control (♦) and then with increasing concentrations of PE as described in the legend to FIG. 2. The mean±standard deviation of three experiments is shown. FIG. 5B depicts the results after aortic rings were incubated with 10 nM Δkringle-scuPA (✕), 10 nM Δkringle-tcuPA (▲) or PBS control (♦) and then with increasing concentrations of PE as described in the legend to FIG. 2. The mean±standard deviation of three experiments is shown.

FIG. 6, comprising FIGS. 6A, 6B and 6C, is a series of graphs depicting binding of scuPA$^{\Delta 136-143}$ to suPAR measured by surface plasmon resonance. The binding of wild type scuPA (FIG. 6A) and scuPA$^{\Delta 136-143}$ (FIG. 6B) to suPAR are shown. Urokinase (12.5 nM to 0.2 nM) was then added in two fold increments (FIG. 6C). An experiment representative of three experiments so performed is shown.

DETAILED DESCRIPTION OF THE INVENTION

Figure 2:
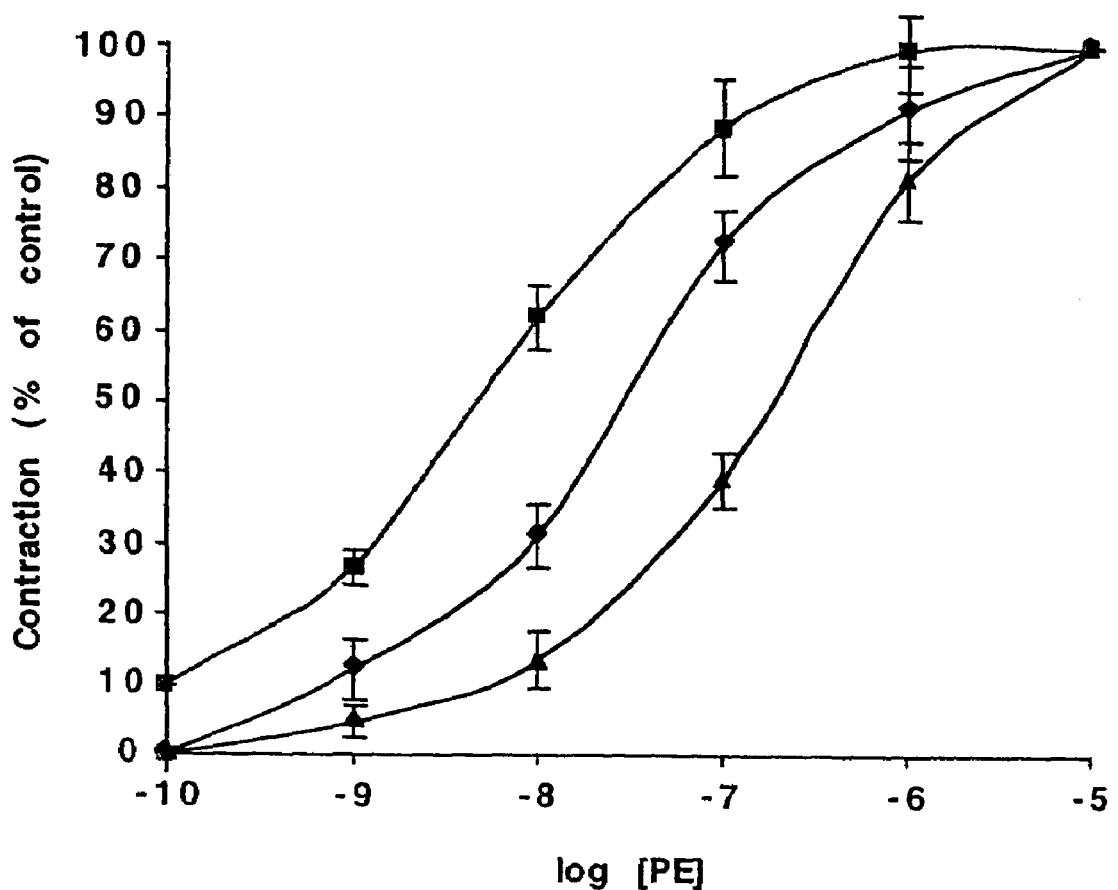
FIG. 2 is a graph depicting the effect of uPA upon the contraction of rat aortic rings in an accumulation curve. The contraction of rat aortic rings was induced by phenylepherine (PE) at the indicted concentrations in the absence (♦) or presence of 10 nM scuPA (▲) or tcuPA (■). In this and in each of the remaining figures, the molar concentration of PE is displayed in logarithmic units. The mean±SD of 6 experiments is shown.

The present invention relates to the finding that several domains of the urokinase-type plasminogen activator (uPA) are effective for modulating the contractility or modulating the angiogenic activity of a mammalian muscle or endothelial cell or tissue. The invention includes compositions and methods for using these uPA domains advantageously to modulate the contractility and/or the angiogenic activity of a mammalian muscle or endothelial cell or tissue in the treatment of a disease or condition having abnormal muscle cell or tissue contractility or abnormal muscle or endothelial cell or tissue angiogenic activity as a symptom thereof, or wherein inducing relaxation of a muscle cell or tissue or modulating angiogenesis would be efficacious to the mammal.

The invention also includes methods for identifying and using binding proteins as well as agonists and antagonists of these domains of uPA in the treatment of a disease or condition having abnormal muscle cell or tissue contractility or abnormal angiogenic activity as a symptom thereof. In addition, agonists or antagonists to the binding proteins are used in the methods of the invention for the treatment of a disease or condition having abnormal muscle cell or tissue contractility or abnormal angiogenic activity as a symptom thereof.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, the term "isolated polypeptide" refers to a polypeptide segment or fragment which has been separated from sequences which flank it in a naturally occurring state, e.g., a polypeptide fragment which has been removed from the sequences which are normally adjacent to the fragment, e.g., the sequences adjacent to the fragment in a protein in which it naturally occurs. The term also applies to a polypeptide which has been substantially purified from other components which naturally accompany the polypeptide, e.g., proteins, RNA or DNA which naturally accompany it in the cell. The term therefore includes, for example, a recombinant polypeptide which is encoded by a nucleic acid incorporated into a vector, into an autonomously replicating plasmid or virus, or into the genomic DNA of a prokaryote or eukaryote, or which exists as a separate molecule (e.g, as a cDNA or a genomic or cDNA fragment produced by polymerase chain reaction (PCR) or restriction enzyme digestion) independent of other sequences. It also includes a recombinant polypeptide which is part of a hybrid polypeptide comprising additional amino acids. Isolated polypeptides are exemplified by the isolated kringle, the isolated growth factor domain, and the isolated ATF, which are described herein.

As used herein, the term "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g, as a cDNA or a genomic or cDNA fragment produced by PCR or restriction enzyme digestion) independent of other sequences. It also includes a recombinant DNA which is part of a hybrid gene encoding additional polypeptide sequence.

As used herein, the term "modulating the contractility" or "to modulate the contractility" of a cell or tissue in the context of the inventive composition means to enhance or disinhibit, or to inhibit the contractility of a cell or tissue, such as, for example, a mammalian smooth muscle cell or tissue, relative to the contractility of an otherwise identical cell or tissue which is not provided the composition of the invention or subjected to the method of the invention. The contraction process of the cell or tissue in which contractility is to be evaluated can be either mediated or not mediated by an inducing compound. When present, the inducing compound is any compound capable of mediating the contraction of a cell, and includes, by way of example and not by limitation, neurotransmitter compounds such as phenylepherine (PE), epinepherine, endothelin and acetylcholine (AC).

As used herein, the term "contractility" in the context of a muscle cell or tissue means any one or more of the propensity of the muscle cell or tissue to contract, the force with which the muscle cell or tissue contracts, the stroke volume of the tissue upon contraction, and the velocity of muscle tissue shortening (i.e. the extent of shortening of a muscle tissue per unit of time).

As used herein, "to enhance or disinhibit the contractility" of a muscle cell or tissue means to increase the contractility of the muscle cell or tissue. By way of example and not by limitation, increasing the contractility of the muscle cell or tissue can encompass any one or more of increasing the force of contraction of the muscle cell or tissue, increasing the stroke volume of the muscle tissue during contraction, increasing the propensity of the muscle cell or tissue to contract by increasing the magnitude or frequency of any signal transduction event or process associated with promoting contraction (e.g. calcium release), and decreasing the amount of an inducing compound required to mediate contraction (e.g. decreasing the $EC_{50}$ of an inducing compound).

As used herein, "to inhibit the contractility" of a muscle cell or tissue means to decrease the contractility of the muscle cell or tissue. By way of example and not by limitation, decreasing the contractility of the muscle cell or tissue can encompass any one or more of decreasing the force of contraction of the muscle cell or tissue, decreasing the stroke volume of the muscle tissue during contraction, decreasing the propensity of the muscle cell or tissue to contract by decreasing or inhibiting the magnitude or the frequency of any signal transduction event or process associated with promoting contraction (e.g. calcium release), and increasing the amount of an inducing compound required to mediate contraction (e.g. increasing the $EC_{50}$ of an inducing compound).

As used herein, the term "angiogenic activity" of a cell or tissue in the context of the methods and compositions of the invention means one or more of the proliferation and migration of a vascular smooth muscle cell involved in the vascularization of a tissue, and the proliferation of an endothelial cell involved in the vascularization of a tissue.

As used herein, the term "modulating angiogenic activity" or "to modulate the angiogenic activity" or "to modulate angiogenesis" of a cell or tissue in the context of the methods and compositions of the invention means to either promote or to inhibit the angiogenic activity of a vascular smooth muscle cell or tissue or a vascular endothelial cell or tissue. To promote angiogenic activity means to increase or enhance the proliferation or migration of a vascular smooth muscle cell or tissue, or to increase or enhance the proliferation of an endothelial cell involved in the vascularization of a tissue. By way of example and not by limitation, a compound which inhibits the proliferation of an endothelial cell involved in vascularization of a tissue or which inhibits the proliferation or migration of a vascular smooth muscle cell (e.g. a compound with an angiostatic activity) modulates the angiogenic activity of a muscle or endothelial cell or tissue by inhibiting the angiogenic activity. Also by way of example and not by limitation, a compound which promotes the proliferation of an endothelial cell involved in vascularization of a tissue or which promotes the proliferation or migration of a vascular smooth muscle cell (e.g. a compound with angiogenic activity) modulates the angiogenic activity of a muscle or endothelial cell or tissue by promoting or enhancing the angiogenic activity.

As used herein, the term "abnormal angiogenic activity" in the context of the invention means an unusually high or an unusually low degree of angiogenic activity in a vascular smooth muscle or vascular endothelial cell or tissue of a mammal relative to an otherwise identical normal vascular smooth muscle or vascular endothelial cell or tissue of a mammal, or a degree of angiogenic activity in a vascular smooth muscle or vascular endothelial cell or tissue of a mammal which is deleterious or disadvantageous to the mammal.

As used herein, the phrase "treating abnormal angiogenic activity" or "treating a disease or condition having abnormal angiogenic activity as a symptom thereof" means to increase or decrease, as appropriate, the angiogenic activity of a vascular smooth muscle cell or tissue or a vascular endothelial cell or tissue having an abnormally low or abnormally high angiogenic activity, or having a degree of angiogenic activity which is deleterious or disadvantageous to the mammal. The phrase also means to alleviate a symptom of the abnormal angiogenic activity, or to reduce the severity of a pathological physiological consequence of the abnormal angiogenic activity in the mammal.

By way of example and not by limitation, where the disease or condition is tumor angiogenesis in a mammal, treating abnormal angiogenic activity in the manunal means to inhibit the endothelial cell proliferation which is required to develop the tumor neovessels which are to supply the growing tumor, lest it outgrow its blood supply. By inhibiting endothelial cell proliferation in this context, the tumor is deprived of the vascularization necessary for continued growth, thereby treating the disease or condition of tumor angiogenesis.

Also, by way of example, and not by limitation, where the disease or condition is an ocular disorder such as a diabetic or sickle cell or other form of ischemic retinopathy, wherein poorly constructed vascular vessels are induced to grow, but are weak and rupture, leading to bleeding and impaired vision, treating abnormal angiogenic activity in the mammal means to promote the endothelial cell proliferation which is required to develop vascular vessels of proper strength to prevent rupture, thereby treating the disease or condition of ischemic retinopathy.

By way of a further example, and not by limitation, where the disease or condition is any one or more of post-coronary angioplasty, carotid endarterectomy, post-cardiac transplant, and atherosclerosis, wherein the proliferation of vascular smooth muscle cells in the media and migration of these cells through the internal elastic lamina into the vascular intima and subsequent proliferation of these cells with concomitant generation of atherogenic lipids occurs, treating abnormal angiogenic activity in the mammal means to inhibit the vascular smooth muscle cell proliferation and migration associated with this phenomenon, thereby treating the disease or condition.

As used herein, the term "abnormal muscle cell or tissue contractility," means a significantly elevated or significantly diminished contractility of a muscle cell or tissue relative to an otherwise identical normal muscle cell or tissue. The degree of elevated or diminished contractility which is to be considered significant will vary with the specific type of muscle cell or tissue tested, as well as the specific type of function evaluated for the muscle cell. The ordinarily skilled artisan will be aware of such variations and the degree of elevated or diminished contractility to be considered significant. The term also includes spastic contraction of a muscle tissue which is either disadvantageous or deleterious to the mammal or which causes discomfort. The spastic contraction can be either naturally occurring or resulting from a surgical procedure.

As used herein, the phrase "treating a disease or condition in a mammal which is characterized by abnormal muscle cell or tissue contractility" means to increase or decrease, as appropriate, the contractility of a muscle cell or tissue having an abnormally low or abnormally high contractility. The phrase also means to reduce the frequency with which the abnormal muscle cell or tissue contractility is experienced by a patient having such a disease or condition, to alleviate a symptom of the abnormal muscle cell or tissue contractility, or to reduce the frequency or severity of a pathological physiological consequence of the abnormal muscle cell or tissue contractility in the mammal.

As used herein, the term "recombinant polynucleotide" refers to a polynucleotide having sequences that are not naturally joined together. An amplified or assembled recombinant polynucleotide may be included in a suitable vector, and the vector can be used to transform a suitable host cell. A recombinant polynucleotide may serve a non-coding function (e.g., promoter, origin of replication, ribosome-binding site, etc.) as well. A host cell that comprises a recombinant polynucleotide is referred to as a "recombinant host cell." A gene which is expressed in a recombinant host cell wherein the gene comprises a recombinant polynucleotide, expresses a "recombinant polypeptide."

As used herein, the term "recombinant polypeptide" means a polypeptide which is produced upon expression of a recombinant polynucleotide.

As used herein, the term "polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

It will be appreciated, of course, that the peptides or polypeptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound as a modulator of one or more of contractility and angiogenic activity of a muscle cell or tissue, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the biological activity of the peptide for modulating one or more of the contractility and angiogenic activity of a muscle or endothelial cell or tissue. Such modifications include, but are not limited to, substittition of one or more of the amino acids in the natural L-isomeric form with amino acids in the D-isomeric form. Thus, the peptide may include one or more D-amino acid residues, or may comprise amino acids which are all in the D-form. Retro-inverso forms of peptides in accordance with the present invention are also contemplated, for example, inverted peptides in which all amino acids are substituted with D-amino acid forms.

Acid addition salts of the peptides are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tartaric, citric, benzoic, cinnamic, mandelic, methanesulfonic, ethanesulfonic, p-toluenesulfonic, salicyclic and the like, to provide a water soluble salt of the peptide is suitable for use as a modulator of one or more of the contractility and angiogenic activity of a muscle or endothelial cell or tissue.

The present invention also includes analogs of polypeptides or peptides of the invention. Analogs can differ from naturally occurring proteins or peptides by conservative amino acid sequence differences or by any of the modifications described above or known in the art which do not affect sequence, or by both. Modifications can be made as described above or by using any technique known to the skilled artisan.

For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a modulator of one or more of the contractility and angiogenic activity of a muscle or endothelial cell or tissue. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

As used herein, an "analog" of a peptide or a polypeptide of the invention means a peptide or polypeptide which has been modified from the naturally occurring peptide or polypeptide by any of the modifications described herein or known to the skilled artisan, but which still exhibits activity similar to the naturally occurring peptide or polypeptide as a modulator of one or more of the contractility and angiogenic activity of a mammalian muscle or endothelial cell or tissue.

As used herein, a "chimeric peptide" or "chimeric polypeptide" means a peptide or polypeptide which comprises at least a portion of a naturally occurring peptide or polypeptide of the invention and at least a portion of a peptide or polypeptide with which it is normally not found together with in nature, but which still exhibits activity similar to the naturally occurring peptide or polypeptide of the invention as a modulator of one or more of the contractility and angiogenic activity of a mammalian muscle or endothelial cell or tissue.

As used herein, a "functional element" of a peptide or a polypeptide of the invention means a portion of a peptide or polypeptide of the invention which participates in the modulation of one or more of the contractility and angiogenic activity of a mammalian muscle or endothelial cell or tissue. A method of identifying a functional element of a peptide or polypeptide of the invention is described herein.

As used herein, an "epitope" of a peptide or a polypeptide of the invention means a portion of a peptide or polypeptide of the invention which is exposed at the surface of the peptide or polypeptide of the invention or which is accessible to a binding protein of a peptide or polypeptide of the invention. A method of identifying a binding protein of a peptide or polypeptide of the invention is described herein.

As used herein, a "binding protein" of a peptide or polypeptide of the invention means a protein or polypeptide which substantially binds to the peptide or polypeptide of the invention, but which does not substantially bind to other peptides or proteins which are associated with the peptide or polypeptide of the invention, wherein the "binding protein" also transmits a biochemical signal or participates in a signal transduction event which mediates the contraction of a muscle cell or which mediates the angiogenic activity of a muscle or endothelial cell. The binding protein can also participate in signal transduction indirectly, by facilitating the interaction of the peptide or polypeptide of the invention with, or by acting in concert with another molecule which provides the proximate signal which mediates muscle cell contraction or muscle or endothelial cell angiogenic activity. By way of example and not by limitation, the binding protein can be a receptor or a transport protein of the peptide or polypeptide of the invention. The binding protein can be any binding protein known or yet to be known, and includes, by way of example and not by limitation, certain beta-integrins as binding proteins which participate in signal transduction directly, and the low-density lipoprotein related protein or the alpha 2 macroglobulin receptor (LRP/α2 macroglobulin receptor) as a binding protein which participates in signal transduction indirectly by down-regulating the signal transduction process.

As used herein, the term "vector" means a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated viral vectors, retroviral vectors, and the like.

As used herein, the term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Description

The invention includes compositions comprising the uPA kringle or the growth factor domain alone, or in combination with one or more other domains of the uPA molecule, in an amount effective to modulate one or more of the contractility of a mammalian muscle cell or tissue and the angiogenic activity of a mammalian muscle or endothelial cell or tissue. The compositions of the invention are useful for the treatment of a disease or condition in a mammal having as a symptom thereof one or more of abnormal muscle cell or tissue contractility and abnormal muscle or endothelial cell or tissue angiogenic activity. The domain or domains of uPA can be present in the inventive compositions and methods either as an isolated polypeptide, as part of the whole uPA molecule in either single chain or two chain form (scuPA or tcuPA, respectively), or as part of a deletion mutant thereof, which lacks either the uPA kringle or the connecting peptide.

The inventive method comprises administering to a mammal afflicted with such a disease or condition an effective amount of an inventive composition, and modulating the contractility and/or the angiogenic activity of the muscle or endothelial cell or tissue, thereby treating the disease or condition. The invention also includes methods for identifying and using binding proteins, agonists and antagonists for one or more domains of uPA to modulate muscle cell or tissue contractility and/or angiogenic activity, as well as using agonists and antagonists to the binding proteins themselves to modulate muscle or endothelial cell or tissue contractility and/or angiogenic activity, thereby treating the disease or condition.

In the methods and compositions of the invention, the disease or condition can be any disease or condition in a mammal in which one or more of abnormal muscle cell or tissue contractility and abnormal angiogenic activity is a symptom. Such diseases and conditions include, by way of example and not by limitation, the following: cardiovascular diseases and conditions such as hypotension, hypertension and atherosclerosis; conditions which promote thrombotic disorders such as stroke, heart attack, microvascular occlusions, thrombotic microangiopathies, and surgically induced thrombotic disorders (i.e. post angioplasty stenting); angiogenic disorders; respiratory diseases and conditions such as pulmonary fibrosis and asthma; invasion, angiogenesis and metastasis of cancer or tumor cells; ocular disorders such as glaucoma and diabetic retinopathy; wound healing disorders, disorders of fibrinolysis and clotting; and reproductive disorders such as uterine contraction disorders and male impotence.

In the methods and compositions of the invention, the cell can be any type of mammalian muscle cell or vascular endothelial cell. Types of muscle cells include a smooth muscle cell, a striated muscle cell and a cardiac muscle cell. Preferably, the cell is a smooth muscle cell. Examples of preferred smooth muscle cells include vascular and bronchial smooth muscle cells.

In preferred embodiments of the invention, the mammalian muscle or endothelial cell is a part of a mammalian muscle tissue, and is in a mammal. Preferably, the inventive composition comprises the one or more domains of uPA in an amount effective to modulate the contractility and/or angiogenic activity of a mammalian muscle or endothelial tissue.

The invention includes a composition comprising the uPA kringle in an amount effective to modulate one or more of the contractility and the angiogenic activity of a mammalian muscle or endothelial cell or tissue. The uPA kringle is a polypeptide portion of the urokinase-type plasminogen activator protein which shares at least about 75% homology with the polypeptide corresponding to SEQ ID NO:1 (FIG. 1A). Preferably, the uPA kringle is about 80% homologous, more preferably about 85% homologous, even more preferably 90% homologous, yet more preferably 95% homologous, and most preferably about 99% homologous to the polypeptide corresponding to SEQ ID NO:1. Even more preferably, the uPA kringle is the polypeptide corresponding to SEQ ID NO:1.

The determination of percent homology (i.e. percent identity) described herein between two amino acid or nucleotide sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877).

This algorithm is incorporated in the NBLAST and XBLAST programs of Altschul, et al. (1990, J. Mol. Biol. 215:403-410), and can be accessed, for example, at the National Center for Biotechnology Information (NCBI) world wide web site "www.ncbi.nlm.nih.gov/BLAST/". BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein.

To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (id.) and relationships between molecules which share a common pattern.

When utilizing BLAST, Gapped BLAST, PSI-Blast, and PHI-Blast, programs, the Default parameters of the respective programs (e.g., XBLAST and NBLAST) can be used. See www.ncbi.nlm.nih.gov.

The percent identity between two amino acid or nucleotide sequences can be determined using techniques similar to those described above, with or without allowing gaps. In calculating percent identity, typically exact matches are counted.

In a preferred embodiment, the uPA kringle is present in an amount effective to enhance or disinhibit the contractility of a mammalian smooth muscle cell or tissue. In another preferred embodiment, the uPA kringle is present in an amount effective to inhibit the angiogenic activity of a vascular smooth muscle cell or tissue or a vascular endothelial cell or tissue.

Preferably, the uPA kringle is present in the inventive composition at a concentration ranging from about ten picomolar to about one hundred micromolar.

In one embodiment, the uPA kringle is present in the inventive composition as an isolated kringle. An isolated kringle is an isolated polypeptide which comprises the uPA kringle. The isolated kringle can be prepared by any method known to the skilled artisan for preparing an isolated polypeptide.

For example, the isolated kringle can be obtained by preparing and purifying a recombinant version of any of the polypeptides described herein which comprise the uPA kringle. Molecular biology techniques for the preparation of recombinant polypeptides are well known in the art, and are described for example in Sambrook et al., 1989, *Molecular Cloning: A Laboratory Manual*, Cold Spring Harbor Laboratory, New York; Ausubel et al., 1994, *Current Protocols in Molecular Biology*, John Wiley & Sons, New York), and Gerhardt et al., eds., 1994, *Methods for General and Molecular Bacteriology*, American Society for Microbiology, Washington, D.C. Protein purification methods are also well known in the art, and are described, for example in Deutscher et al. (ed., 1990, *Guide to Protein Purification*, Harcourt Brace Jovanovich, San Diego).

In a preferred aspect, the isolated kringle is prepared by performing a limited proteolysis of scuPA, then purifying the resulting polypeptide using reverse-phase HPLC, as described herein in the Examples.

The invention also includes a composition comprising the uPA growth factor domain in an amount effective to modulate the contractility and/or the angiogenic activity of a mammalian muscle or endothelial cell. The growth factor domain is a polypeptide portion of the urokinase-type plasminogen activator protein which shares at least about 75% homology with the polypeptide corresponding to SEQ ID NO:2 (FIG. 1B). Preferably, the growth factor domain is about 80% homologous, more preferably about 85% homologous, even more preferably 90% homologous, yet more preferably 95% homologous, and most preferably about 99% homologous to the polypeptide corresponding to SEQ ID NO:2. Even more preferably, the growth factor domain is the polypeptide corresponding to SEQ ID NO:2.

In a preferred embodiment, the uPA growth factor domain is present in an amount effective to inhibit the contractility of a mammalian smooth muscle cell or tissue. Preferably, the uPA growth factor domain is present in the inventive composition at a concentration ranging from about 10 picomolar to about 100 micromolar.

In one embodiment, the growth factor domain is present in the inventive composition as an isolated growth factor domain. An isolated growth factor domain is an isolated polypeptide which comprises the uPA growth factor domain. The isolated growth factor domain can be prepared by any method known to the skilled artisan for preparing an isolated polypeptide. For example, the isolated growth factor domain can be obtained by preparing and purifying a recombinant version of any of the polypeptides described herein which comprise the growth factor domain. Molecular biology techniques for the preparation of recombinant polypeptides are well known in the art, and are discussed above.

In other embodiments, the inventive composition comprises, in addition to the uPA kringle or the growth factor domain, one or more additional domains of the uPA protein selected from the group consisting of the connecting peptide, the protease domain, the uPA kringle and the growth factor domain.

In one aspect, the composition of the invention comprises the full uPA protein. The full uPA protein comprises, from the N-terminal end to the C-terminal end, respectively, the growth factor domain, the kringle, the connecting peptide, and the protease domain. The full uPA protein is a polypeptide which shares at least about 75% homology with the polypeptide corresponding to SEQ ID NO:3 (FIG. 1C). Preferably, the full uPA protein is about 80% homologous, more preferably about 85% homologous, even more preferably 90% homologous, yet more preferably 95% homologous and most preferably about 99% homologous to the polypeptide corresponding to SEQ ID NO:3. Even more preferably, the full uPA protein is the polypeptide corresponding to SEQ ID NO:3.

The inventive composition can comprise the full uPA protein in nascent form, which is termed single chain urokinase (scuPA). Single chain urokinase (scuPA) is the form of the urokinase-type plasminogen activator protein which is synthesized by mammalian cells as the parent molecule. In this embodiment, the growth factor domain of scuPA is present in an amount effective to inhibit the contractility of a mammalian muscle cell. Preferably, the growth factor domain is present in an amount effective to cause a dose-dependent inhibition of acetylcholine induced contraction of a bronchial smooth muscle cell.

The molecule scuPA is capable of being converted by either an autoactivation or by a protease to a form termed two chain urokinase (tcuPA). Proteases capable of converting scuPA to tcuPA include plasmin and kallikrein. The two chain form of urokinase is produced by proteolytic cleavage of scuPA between amino acid residues number 158 and 159 of the full uPA protein, and the resulting tcuPA molecule is held together in two chain form by disulfide bonds.

In another aspect, the inventive composition comprises tcuPA, a polypeptide which shares at least about 75% homology with the polypeptide corresponding to SEQ ID NO:3 (FIG. 1C). Preferably, tcuPA is about 80% homologous, more preferably about 85% homologous, even more preferably 90% homologous, yet more preferably 95% homologous, and most preferably about 99% homologous to the polypeptide corresponding to SEQ ID NO:3. Even more preferably, tcuPA is the polypeptide corresponding to SEQ ID NO:3. In this embodiment, tcuPA is present in an amount effective to modulate the contractility of a mammalian muscle cell.

In one preferred aspect, the uPA kringle is present in the inventive composition in an amount effective to enhance or disinhibit PE-induced contraction of a mammalian vascular smooth muscle cell or tissue.

In another preferred aspect, the uPA kringle is present in the inventive composition in an amount effective to inhibit AC-induced contraction of a mammalian bronchial smooth muscle cell or tissue.

In another embodiment, the inventive composition comprises the amino terminal fragment of uPA (ATF). The ATF is a polypeptide portion of the full uPA protein which comprises the growth factor domain and the uPA kringle. The ATF shares at least about 75% homology with the polypeptide corresponding to SEQ ID NO:4 (FIG. 1D). Preferably, the ATF is about 80% homologous, more preferably about 85% homologous, even more preferably 90% homologous, yet more preferably 95% homologous, and most preferably about 99% homologous to the polypeptide corresponding to SEQ ID NO:4. Even more preferably, the ATF is the polypeptide corresponding to SEQ ID NO:4.

In embodiments of the inventive composition comprising the ATF, the ATF is present in an amount effective to modulate the contractility or angiogenic activity of a mammalian muscle or endothelial cell or tissue. Preferably, the uPA kringle of ATF is present in the inventive composition in an amount effective to enhance or disinhibit PE-induced contraction of a mammalian vascular smooth muscle cell or tissue or in an amount effective to inhibit the angiogenic activity of a vascular smooth muscle cell or tissue or a vascular endothelial cell or tissue.

In one embodiment, the ATF is present in the inventive composition as an isolated ATF. An isolated ATF is an isolated polypeptide which comprises the uPA kringle and the uPA growth factor domain. The isolated ATF can be prepared by any method known to the skilled artisan for preparing an isolated polypeptide. For example, the isolated ATF can be obtained by preparing and purifying a recombinant version of any of the polypeptides described herein which comprise the ATF. Molecular biology techniques for the preparation of recombinant polypeptides are well known in the art, and are discussed above.

Preferably, the isolated ATF is prepared by autodigestion of tcuPA. In another preferred aspect, where the polypeptide of the invention comprises both the ATF and the connecting peptide, the polypeptide is prepared by matrilysin (MMP-7) or stromelysin (MMP-3) digestion of uPA.

In any of the compositions and methods of the invention described herein, a functional element, an analog, an epitope, or a chimeric peptide can be used in place of one or more of the isolated uPA kringle, the isolated growth factor domain and the isolated ATF. This enables the use of a smaller polypeptide in the inventive compositions having similar or greater activity than the corresponding larger isolated polypeptide for modulating muscle cell contractility or angiogenic activity. Methods for identifying a functional element, an epitope, an analog or a chimeric polypeptide for any of these isolated polypeptides are described herein and known in the art. By way of example and not by limitation, such functional elements, analogs, epitopes and chimeric peptides can be prepared using recombinant technology or isolated from natural sources. Alternatively, they can be prepared synthetically by using any polypeptide synthesis method known in the art, such as a solid-phase polypeptide synthesis method.

The invention also includes a composition comprising a polypeptide which comprises the connecting peptide and the protease domains of uPA, in an amount effective to modulate the contractility of a mammalian muscle cell or tissue. This polypeptide is termed LMW-uPA, and shares at least about 75% homology with the polypeptide corresponding to SEQ ID NO:5 (FIG. 1E). Preferably, the LMW-uPA is about 80% homologous, more preferably about 85% homologous, even more preferably 90% homologous, yet more preferably 95% homologous, and most preferably about 99% homologous to the polypeptide corresponding to SEQ ID NO:5. Even more preferably, the LMW-uPA is the polypeptide corresponding to SEQ ID NO:5.

In a preferred embodiment, the LMW-uPA is present in the inventive composition in an amount effective to inhibit the contractility of a mammalian smooth muscle cell or tissue.

The invention also includes a composition comprising a polypeptide deletion mutant of either scuPA or tcuPA in which the connecting peptide has been deleted. Methods for preparing deletion mutants of wild type polypeptides are known in the art, and a preferred method is described herein in the Examples.

In one embodiment, a uPA deletion mutant lacking the connecting peptide (scuPA$^{\Delta 136-143}$) is present in the inventive composition in an amount effective to modulate the contractility and/or the angiogenic activity of a mammalian muscle or endothelial cell. The scuPA$^{\Delta 136-143}$ shares at least about 75% homology with the polypeptide corresponding to SEQ ID NO:6 (FIG. 1F). Preferably, the uPA deletion mutant is about 80% homologous, more preferably about 85% homologous, even more preferably 90% homologous, yet more preferably 95% homologous and most preferably about 99% homologous to the polypeptide corresponding to SEQ ID NO:6. Even more preferably, the uPA deletion mutant is the polypeptide corresponding to SEQ ID NO:6.

In a preferred embodiment, scuPA$^{\Delta 136-143}$ is present in the inventive composition in an amount effective to enhance or disinhibit the contractility of a mammalian smooth muscle cell.

The invention also includes a composition comprising a polypeptide deletion mutant of either scuPA or tcuPA in which the uPA kringle has been deleted. Methods for preparing deletion mutants of wild type polypeptides are known in the art, and a preferred method is described herein in the Examples.

In one embodiment, a uPA deletion mutant of scuPA or tcuPA lacking the uPA kringle (Δkringle-scuPA or Δkringle-tcuPA) is present in the inventive composition in an amount effective to modulate the contractility and/or the angiogenic activity of a mammalian muscle or endothelial cell. The Δkringle-scuPA shares at least about 75% homology with the polypeptide corresponding to SEQ ID NO:7 (FIG. 1G). Preferably, the uPA deletion mutant is about 80% homologous, more preferably about 85% homologous, even more preferably 90% homologous, yet more preferably 95% homologous and most preferably about 99% homologous to the polypeptide corresponding to SEQ ID NO:7. Even more preferably, the uPA deletion mutant is the polypeptide corresponding to SEQ ID NO:7.

In a preferred embodiment, one or more of Δkringle-scuPA and Δkringle-tcuPA is present in the inventive composition in an amount effective to inhibit the contractility of a mammalian smooth muscle cell and to proteolytically activate plasminogen.

In another embodiment, the inventive composition comprises a polypeptide comprising the ATF and the connecting peptide in an amount effective to modulate one or more of the contractility and angiogenic activity of a mammalian muscle or endothelial cell or tissue. In this aspect, the polypeptide comprising the ATF and the connecting peptide shares at least about 75% homology with the polypeptide corresponding to SEQ ID NO:8 (FIG. 1H). Preferably, the polypeptide is about 80% homologous, more preferably about 85% homologous, even more preferably 90% homologous, yet more preferably 95% homologous, and most preferably about 99% homologous to the polypeptide corresponding to SEQ ID NO:8. Even more preferably, the polypeptide is the polypeptide corresponding to SEQ ID NO:8. Without wishing to be bound by any one theory, it is suspected that the connecting peptide domain, when present in the same polypeptide with the ATF, results in a polypeptide which is more effective at modulating angiogenic activity than the ATF alone, possibly by affecting cell adhesion.

The invention also includes a composition comprising a polypeptide which comprises the uPA kringle and the connecting peptide, in an amount effective to modulate one or more of the contractility and the angiogenic activity of a mammalian muscle or endothelial cell or tissue. This polypeptide shares at least about 75% homology with the polypeptide corresponding to SEQ ID NO:9 (FIG. 1I). Preferably, the polypeptide is about 80% homologous, more preferably about 85% homologous, even more preferably 90% homologous, yet more preferably 95% homologous, and most preferably about 99% homologous to the polypeptide corresponding to SEQ ID NO:9. Even more preferably, the polypeptide is the polypeptide corresponding to SEQ ID NO:9.

In another embodiment, any of the compositions of the invention described above can further comprise an inducing compound present in an amount effective to mediate contraction of a mammalian muscle cell. The inducing compound can be any compound capable of mediating the contraction of a mammalian muscle cell, and includes, by way of example and not by limitation, neurotransmitter compounds such as phenylepherine (PE), acetylcholine (AC), epinepherine and endothelin. The amount of such compounds to be effective for mediating contraction of a mammalian muscle cell will be apparent to the skilled artisan.

In another embodiment, the inventive composition comprises any of the compositions of the invention described above, and further comprises one or more compounds suitable for one or more of promoting, enhancing, prolonging and amplifying the effectiveness of the composition of the invention for modulating the contractility and/or the angiogenic activity of a mammalian muscle or endothelial cell or tissue. In one aspect, the one or more compounds are selected from the group consisting of agonists, antagonists and binding proteins of any one or more domains of uPA. Methods of identifying agonists, antagonists and binding proteins to one or more domains of uPA are described herein. Also, the one or more compounds can be agonists or antagonists to the binding proteins themselves.

The invention also includes an isolated nucleic acid encoding a polypeptide comprising one or more of the domains of uPA described herein. The isolated nucleic acid shares at least about 75% homology, preferably about 80% homology, more preferably about 85% homology, even more preferably about 90% homology, yet more preferably 95% homology, and most preferably about 99% homology with a nucleic acid selected from the group consisting of SEQ ID NO:10 (FIG. 1J), SEQ ID NO:11 (FIG. 1K), SEQ ID NO:12 (FIG. 1L), SEQ ID NO:13 (FIG. 1M), SEQ ID NO:14 (FIG. 1N), SEQ ID NO:15 (FIG. 1O), SEQ ID NO:16 (FIG. 1P), SEQ ID NO:17 (FIG. 1Q) and SEQ ID NO:18 (FIG. 1R). Even more preferably, the nucleic acid is selected from the group consisting of SEQ ID NO:10-SEQ ID NO:18. In this embodiment of the invention, the isolated nucleic acid is present in an amount effective to transform a mammalian muscle or endothelial cell to provide transgene expression of the one or more polypeptide domains of uPA at a level of expression effective to modulate the contractility and/or angiogenic activity of the mammalian muscle or endothelial cell so transfected.

The isolated nucleic acid can be either alone as a "naked" nucleic acid, such as a linearized nucleic acid, or as a component of any type of vector suitable for transfecting a mammalian muscle or endothelial cell described herein or known in the art. Preferably, the isolated nucleic acid is a recombinant polynucleotide component of a viral or plasmid expression vector suitable for transfecting a mammalian muscle or endothelial cell, and is operably linked to the appropriate regulatory elements to provide a high level of expression of the transgene once a targeted mammalian muscle or endothelial cell is transformed with the isolated nucleic acid. Examples of preferred vectors include adenovirus, retrovirus, lentivirus and adeno-associated virus vectors. Techniques for using such vectors to transfect a mammalian muscle or endothelial cell are known in the art.

When any one of the polypeptides described herein comprising one or more domains of uPA are to be administered to a mammal or to a tissue of a mammal for the purpose of exerting a beneficial effect in the mammal, the invention should be construed to include delivery of the polypeptide via delivery of an isolated nucleotide sequence encoding the peptide. Expression of the peptide from the nucleotide sequence so delivered to the desired tissue is effective administration of the peptide to the tissue.

In another embodiment, the inventive composition is in the form of a pharmaceutical composition comprising a pharmaceutically acceptable carrier. Such a pharmaceutical composition may consist of the inventive composition alone as the active ingredient, in a form suitable for administration to a subject, or the pharmaceutical composition may comprise the inventive composition as the active ingredient and one or more pharmaceutically acceptable carriers, one or more additional ingredients, or some combination of these. The active ingredient may be present in the pharmaceutical composition in the form of a pharmaceutically acceptable salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "pharmaceutically acceptable salt" means a salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to any mammal. Modification of pharmaceutical compositions suitable for administration to humans in order to render the compositions suitable for administration to various mammals is well understood, and the ordinarily skilled veterinary pharmacologist can design and perform such modification with merely ordinary, if any, experimentation.

Pharmaceutical compositions that are useful in the methods of the invention may be prepared, packaged, or sold in formulations suitable for any route of administration known to the skilled artisan, including, by way of example and not by limitation, oral, parenteral, topical, ocular, inhalation, intrauterine, intravesicular, intraurethral and buccal routes of administration. The pharmaceutical composition can be administered to a mammal by any route of administration known to the skilled artisan, such as those described above, and by any method of administering a pharmaceutical composition to a mammal known in the art. A pharmaceutical composition of the invention may be prepared, packaged, or sold in bulk, as a single unit dose, or as a plurality of single unit doses.

As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrastemal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically dosages of the composition of the invention which may be administered to an animal, preferably a human, range in amount from 1 microgram to about 100 grams per kilogram of body weight of the animal. While the precise dosage administered will vary depending upon any number of factors, including but not limited to, the type of animal and type of disease state being treated, the age of the animal and the route of administration. Preferably, the dosage of the composition will vary from about 1 mg to about 10 g per kilogram of body weight of the animal. More preferably, the dosage will vary from about 10 mg to about 1 g per kilogram of body weight of the animal.

The composition may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

The invention also includes a method of treating a disease or condition in a mammal which has as a symptom thereof one or more of abnormal muscle cell or tissue contractility and abnormal muscle or endothelial cell or tissue angiogenic activity. The components used in the method of the invention are the same as those described above in the inventive compositions. The mammal can be any mammal described in the inventive compositions, but is preferably a human. The muscle or endothelial cell or tissue can be any of the mammalian cell or tissue types described in the inventive compositions. A preferred muscle cell is a smooth muscle cell.

The diseases or conditions in a mammal which can be treated by the method of the invention are the same diseases and conditions described above in the inventive compositions. By way of example and not by limitation, the method of the invention can be used to treat cardiovascular diseases and conditions such as hypotension, hypertension and atherosclerosis; conditions which promote thrombotic disorders such as stroke, heart attack, microvascular occlusions, thrombotic microangiopathies, and surgically induced thrombotic disorders (i.e. post angioplasty stenting); angiogenic disorders; respiratory diseases and conditions such as pulmonary fibrosis and asthma; invasion, angiogenesis and metastasis of cancer or tumor cells; ocular disorders such as glaucoma and diabetic retinopathy; wound healing disorders, disorders of fibrinolysis and clotting; and reproductive disorders such as uterine contraction disorders and male impotence.

In the method of the invention, any of the inventive compositions can be administered to the mammal to be treated by any route of administration known in the art or described herein. In one aspect, the inventive composition is administered to the mammal in the form of a pharmaceutical composition. The pharmaceutical composition can be any of the pharmaceutical compositions described herein in the inventive compositions.

In the method of the invention, any of the compositions of the invention may comprise an inducer compound in an amount effective to mediate the contraction of a mammalian muscle cell. The inducer compound can be any of those described in the inventive compositions.

Also, in the method of the invention, any of the compositions of the invention may further comprise one or more compounds known in the art to enhance and facilitate drug administration. Other possible formulations, such as nanoparticles, liposomes, resealed erythrocytes, and immunologically based systems such as antibody targeting systems may also be used to administer the inventive composition according to the methods of the invention.

The method comprises administering to a mammal afflicted with such a disease or condition a composition comprising the uPA kringle in an amount effective to modulate one or more of the contractility and the angiogenic activity of a mammalian muscle or endothelial cell or tissue. In one aspect, the uPA kringle shares at least about 75% homology with a polypeptide having the amino acid sequence corresponding to SEQ ID NO:1. The uPA kringle component of the inventive composition can be obtained from any of the natural or recombinant sources described herein in the inventive compositions.

In one embodiment, the composition administered to the mammal comprises the uPA kringle as an isolated kringle in an amount effective to modulate one or more of the contractility and the angiogenic activity of a mammalian muscle or endothelial cell or tissue. The isolated kringle can be prepared by any method described herein or known to the skilled artisan.

In another embodiment, the composition administered to the mammal comprises the uPA kringle as part of a polypeptide which shares at least about 75% homology with a polypeptide having the amino acid sequence selected from the group consisting of SEQ ID NO:3 (tcuPA), SEQ ID NO:4 (ATF), SEQ ID NO:6 (scuPA$^{\Delta 136\text{-}143}$), SEQ ID NO:8 and SEQ ID NO:9. The uPA kringle is present in the composition in an amount effective to modulate one or more of the contractility and the angiogenic activity of a mammalian muscle or endothelial cell or tissue.

In yet another embodiment, the composition comprises, in place of the uPA kringle, one or more of a functional element thereof, an epitope thereof, an analog thereof and a chimeric polypeptide thereof, in an amount effective to modulate one or more of the contractility and the angiogenic activity of a mammalian muscle or endothelial cell.

In a further embodiment, the composition of the invention administered to the mammal further comprises, in addition to the uPA kringle (or the one or more functional element thereof, epitope thereof, analog thereof and chimeric polypeptide thereof), one or more of an agonist of the uPA kringle, an agonist of a binding protein of the uPA kringle, an antagonist of the uPA growth factor domain, an antagonist of the connecting peptide, an antagonist of a binding protein of the uPA growth factor domain, and an antagonist of a binding protein of the connecting peptide. These agonists, antagonists and binding proteins are described herein below.

The inventive method also includes modulating one or more of the contractility and the angiogenic activity of the muscle or endothelial cell or tissue having one or more of abnormal contractility and abnormal angiogenic activity. The contractility and/or angiogenic activity of the muscle or endothelial cell or tissue can be either enhanced, disinhibited, or inhibited, relative to an otherwise identical muscle or endothelial cell or tissue in the mammal which is not provided the inventive composition. By modulating one or more of the contractility and the angiogenic activity of the muscle or endothelial cell or tissue, the disease or condition in the mammal is treated.

By way of example and not by limitation, where the disease or condition treated is tumor angiogenesis in a mammal, the angiogenic activity in the mammal is modulated by inhibiting the endothelial cell proliferation which is required to develop the tumor neovessels which are to supply the growing tumor, lest it outgrow its blood supply. By inhibiting endothelial cell proliferation in this context, the tumor is deprived of the vascularization necessary for continued growth, thereby treating the disease or condition of tumor angiogenesis.

Also, by way of example, and not by limitation, where the disease or condition treated is an ocular disorder such as a diabetic or sickle cell or other form of ischemic retinopathy, wherein poorly constructed vascular vessels are induced to grow, but are weak and rupture, leading to bleeding and impaired vision, the angiogenic activity in the mammal is modulated by enhancing the endothelial cell proliferation which is required to develop vascular vessels of proper strength to prevent rupture, thereby treating the disease or condition of ischemic retinopathy.

By way of a further example, and not by limitation, where the disease or condition treated is any one or more of post-coronary angioplasty, carotid endarterectomy, post-cardiac transplant, and atherosclerosis, wherein the proliferation of vascular smooth muscle cells in the media and migration of these cells through the internal elastic lanina into the vascular intima and subsequent proliferation of these cells with concomitant generation of atherogenic lipids occurs, the angiogenic activity in the mammal is modulated by inhibiting the vascular smooth muscle cell proliferation and migration associated with this phenomenon, thereby treating the disease or condition.

Also by way of example, and not by limitation, where the disease or condition in the mammal sought to be prevented is congestive heart failure (CHF), the contractility of cardiac muscle tissue is modulated by inhibiting tonic contraction of cardiac muscle tissue, thereby preventing the development of CHF. In contrast, where CHF has already developed, the CHF is treated by enhancing the contractility of cardiac muscle tissue in order to increase the stroke volume upon contraction of the cardiac muscle tissue.

A further non-limiting example, where the disease or condition treated in the mammal is either an inherited or an acquired dystrophic condition of a skeletal muscle tissue, the contractility of the skeletal muscle tissue is modulated by enhancing the contractility of the skeletal muscle tissue in order to increase or preserve muscle power, thereby treating the disease. In contrast, where the disease or condition treated involves skeletal muscle spasms which are deleterious, disadvantageous, or create discomfort in a mammal, the contractility of the affected skeletal muscle tissue is modulated by inhibiting the contractility of the skeletal muscle tissue.

In the following additional non-limiting examples, where the disease or condition treated in the mammal has as a symptom thereof abnormally high contractility of a smooth muscle cell or tissue, the contractility is modulated by inhibiting the contractility of the affected smooth muscle cell or tissue. By way of example and not by limitation, for abnormal uterine contraction such as premature labor, the contractility of uterine smooth muscle tissue is inhibited; for male impotence, the contractility of vascular smooth muscle tissue is inhibited to promote vasodilation; for angina, the contractility of vascular smooth muscle tissue is inhibited to promote vasodilation; for any type of inherited or acquired cause of thrombosis associated with premature fetal demise or spontaneous abortion, wherein the pathophysiology involves thrombosis/vascular contraction (including eclampsia), the contractility of vascular smooth muscle tissue is inhibited to promote vasodilation and to increase blood flow to the fetus; for asthma or for primary or secondary pulmonary hypertension, the contractility of vascular smooth muscle tissue is inhibited to promote vasodilation; for enhancing delivery of a thrombolytic agent to any part of the cardiovascular system of a mammal the contractility of vascular smooth muscle tissue is inhibited to promote vasodilation; and for inhibiting the spastic contraction of vascular smooth muscle tissue after vascular intervention such as after angioplasty, endarterectomy, thrombectomy br other vascular interventions, the contractility of vascular smooth muscle tissue is inhibited to reduce the frequency and intensity of the spastic contractions and to promote vasodilation.

In one preferred embodiment, the uPA kringle or functional element thereof, epitope thereof, analog thereof or chimeric polypeptide thereof is administered to the mammal in an amount effective to enhance or disinhibit the contractility of a mammalian smooth muscle cell or tissue and/or in an amount effective to inhibit the angiogenic activity of a vascular smooth muscle or vascular endothelial cell or tissue. Preferably, the smooth muscle cell or tissue is a vascular smooth muscle cell or tissue and the disease or condition treated is one or more of hypotension and cancer or tumor cell invasion, angiogenesis, growth and metastasis.

The invention also includes a method for treating a mammal afflicted with a disease or condition having as a symptom thereof one or more of abnormal contractility and abnormal angiogenic activity. The method comprises administering to the mammal a composition comprising the uPA growth factor domain in an amount effective to modulate one or more of the contractility and the angiogenic activity of a mammalian muscle or endothelial cell or tissue. In one aspect, the uPA growth factor domain shares at least about 75% homology with a polypeptide having the amino acid sequence corresponding to SEQ ID NO:2. The uPA growth factor domain component of the inventive composition can be obtained from any of the natural or recombinant sources described herein in the inventive compositions.

In one embodiment, the composition administered to the mammal comprises the uPA growth factor domain as an isolated growth factor domain in an amount effective to modulate one or more of the contractility and the angiogenic activity of a mammalian muscle or endothelial cell or tissue. The isolated growth factor domain can be prepared by any method described herein or known to the skilled artisan.

In another embodiment, the composition administered to the mammal comprises the uPA growth factor domain as part of a polypeptide which shares at least about 75% homology with a polypeptide having the amino acid sequence selected from the group consisting of SEQ ID NO:3 (scuPA), SEQ ID NO:4 (ATF), SEQ ID NO:6 (scuPA$^{\Delta 136-143}$), SEQ ID NO:7 (Δkringle-scuPA or Δkringle-tcuPA) and SEQ ID NO:8). The uPA growth factor domain is present in the polypeptide in an amount effective to modulate one or more of the contractility and the angiogenic activity of a mammalian muscle or endothelial cell or tissue.

In yet another embodiment, the composition comprises, in place of the uPA growth factor domain, one or more of a functional element thereof, an epitope thereof, an analog thereof and a chimeric polypeptide thereof, in an amount effective to modulate one or more of the contractility and the angiogenic activity of a mammalian muscle or endothelial cell or tissue.

In a further embodiment, the composition of the invention administered to the mammal further comprises, in addition to the uPA growth factor domain (or the one or more functional element thereof, epitope thereof, analog thereof and chimeric polypeptide thereof), one or more of an agonist of the uPA growth factor domain, an agonist of the connecting peptide, an agonist of a binding protein of the growth factor domain, an agonist of a binding protein of the connecting peptide, an antagonist of the uPA kringle, and an antagonist of a binding protein of the uPA kringle. These agonists, antagonists and binding proteins are described herein below.

The inventive method also includes one or more of modulating the contractility and modulating the angiogenic activity of the muscle or endothelial cell or tissue having one or more of abnormal contractility and abnormal angiogenic activity. The contractility of the muscle cell or tissue can be either inhibited, disinhibited or enhanced, relative to an otherwise identical muscle cell or tissue in the mammal which is not provided the inventive composition. By modulating one or more of the contractility and the angiogenic activity of the muscle or endothelial cell or tissue, the disease or condition in the mammal is treated.

In one preferred aspect, the uPA growth factor domain or functional element thereof, epitope thereof, analog thereof or chimeric polypeptide thereof is administered to the mammal in an amount effective to inhibit the contractility of a mammalian smooth muscle cell or tissue and/or to modulate the angiogenic activity of the smooth muscle or endothelial cell. In one preferred aspect, the smooth muscle cell or tissue is a vascular smooth muscle cell or tissue and the disease or condition treated is hypertension.

Optionally, the inventive method can include providing the inventive composition to the interior of a muscle or endothelial cell or tissue having abnormal contractility and/or abnormal angiogenic activity. The inventive composition can be provided to the cell or tissue either alone in "naked" form, for example as an isolated polypeptide, or formulated in a vehicle suitable for delivery, such as, by way of example and not by limitation, in a complex with a cationic molecule or a liposome forming lipid, in a vector, or as a component of a pharmaceutical composition. Such vehicles are well known to the skilled artisan.

The inventive composition can be provided to the cell either directly, by contacting the inventive composition with the cell sought to be modulated, or indirectly, such as through the action of any biological process. By way of example and not by limitation, the inventive composition can be provided to the cell by using a liposome, by contacting the composition with the cell, by transfecting the cell using a vector, by injecting the composition into a tissue or fluid surrounding the cell, by simple diffusion of the composition across the cell membrane, or by any active or passive transport mechanism across the cell membrane. In addition, any of the methods known in the art for providing targeted or in situ delivery of the inventive composition to the interior of a desired cell or to a targeted tissue can be used. By way of example and not by limitation, antibody targeting is one of such methods.

In embodiments of the inventive method where the disease or condition in the mammal sought to be treated is a respiratory disease or condition having as a symptom thereof abnormally high bronchial smooth muscle cell contractility (i.e. excessive bronchoconstriction), the inventive method comprises administering an inventive composition to the mammal which is effective at inhibiting the acetylcholine (AC) mediated contraction of a bronchial smooth muscle cell or tissue. Inventive compositions comprising the uPA kringle as an isolated kringle or as a part of the ATF, tcuPA or the deletion mutant scuPA$^{\Delta 136-143}$ are capable of inhibiting the contractility of a bronchial smooth muscle cell or tissue, and thus are potent bronchodilators which can be used to treat such respiratory diseases or conditions. Examples of preferred respiratory diseases and conditions in this embodiment include asthma, adult respiratory distress syndrome, primary pulmonary hypertension, microvascular thrombotic occlusion and disorders associated with chronic intrapulmonary fibrin formation.

In contrast, in embodiments of the inventive method where the disease or condition in the mammal sought to be treated is characterized by abnormally low vascular smooth muscle cell or tissue contractility (e.g., hypotension) the uPA kringle is administered as part of an inventive composition capable of enhancing PE-induced contraction of a mammalian vascular smooth muscle cell or tissue. For example, in these embodiments, the uPA kringle is administered as an isolated kringle or as a part of a polypeptide of the invention such as ATF, tcuPA, scuPA$^{\Delta 136-143}$, ATF+connecting peptide or uPA kringle+connecting peptide.

In other embodiments, where the disease or condition of the mammal sought to be treated is characterized by abnormally high vascular smooth muscle cell or tissue contractility (e.g., hypertension), the inventive method comprises administering to the mammal an inventive composition comprising the uPA growth factor domain as an isolated growth factor domain, or as a part of a polypeptide of the invention such as scuPA or Δkringle-scuPA or Δkringle-tcuPA, in an amount effective to inhibit PE-induced contraction of a vascular smooth muscle cell or tissue.

The invention also includes a method of identifying a compound which is an agonist or antagonist of one or more of the uPA kringle or a binding protein thereof, the uPA growth factor domain or a binding protein thereof, and the connecting peptide or a binding protein thereof, upon the contractility or angiogenic activity of a mammalian muscle or endothelial cell or tissue. The compound can be any type of compound, and includes by way of example and not by limitation, a drug, a peptide, a polypeptide, a protein, an oligonucleotide, a nucleic acid, a ligand, and an antibody.

The agonist can be any compound capable of enhancing, amplifying or promoting the effect of the domain of uPA or binding protein thereof upon the contractility or angiogenic activity of a mammalian muscle or endothelial cell or tissue.

The agonist can also be any compound which is capable of enhancing, amplifying or promoting a transduction pathway or degradation pathway of the domain of uPA or binding protein thereof. The antagonist can be any compound which is a competitive inhibitor or other inhibitor of the effect of the domain of uPA or binding protein thereof upon the contractility or angiogenic activity of a mammalian muscle or endothelial cell or tissue. The antagonist can also be any compound which is a competitor or inhibitor of a transduction pathway or degradation pathway of the domain of uPA or binding protein thereof. The binding protein can be any protein capable of specifically binding with one or more domains of uPA.

The method comprises assessing the contractility or angiogenic activity of a first mammalian muscle or endothelial cell and an otherwise identical second mammalian muscle or endothelial cell. The contractility or angiogenic activity of the cells can be assessed by any method known in the art or described herein for evaluating the contractility or angiogenic activity of a muscle or endothelial cell or tissue. A preferred method for assessing contractility is described herein in the experimental Examples.

The angiogenic activity of the cells and the effectiveness of a test compound for modulating angiogenic activity can be assessed by examining the growth and migration of cultured endothelial cells or smooth muscle cells in progressively less luxurious media and in response to known chemotactic agents in vitro in the presence or absence of test compound. Cultures can be wounded, and the proliferation and capacity of cells to repair the wound in the presence or absence of test compound can be examined by assays known in the art. In vitro assays can be used such as placing growth factors in subcutaneous pockets of laboratory animals and measuring the ingrowth of vessels. One assay known in the art involves the use of chicken allantoic membranes (CAMs), where CAMs are implanted, and the vessel growth in response to locally infused agents for promoting angiogenesis is measured. A test compound can also be administered to an animal with a spontaneous or implanted tumor, and the angiogenic response of the tumor is evaluated by evaluating its vasculature.

The method thereafter comprises providing to the first cell and the second cell a composition of the invention comprising one or more of the uPA kringle, the uPA growth factor domain and the connecting peptide, in an amount effective to modulate the contractility or angiogenic activity of a mammalian muscle or endothelial cell or tissue. The composition is provided to the first and second cells by any method of providing a composition to a cell described herein. The composition need not be provided to the interior of the cells, but instead, where the first and second cells are in a mammal or in a tissue, the composition of the invention need only be provided to the vascular system of the tissue or mammal.

The method also includes providing to the first cell a compound suspected to be an agonist or antagonist of one or more of the uPA kringle or a binding protein thereof, the uPA growth factor domain or a binding protein thereof, and the connecting peptide or a binding protein thereof, upon the contractility or angiogenic activity of a mammalian muscle or endothelial cell or tissue. The compound is provided to the first cell by any of the methods described herein or known in the art for providing a composition or compound to a cell. The compound need not be provided to the interior of the cell, since a binding protein of the uPA kringle, the uPA growth factor domain, and the connecting peptide can be found either inside or outside of the cell (i.e., as a soluble protein). The compound is provided to the first cell in an amount suspected to be effective to modulate the effect of the composition of the invention upon the contractility or angiogenic activity of a mammalian muscle or endothelial cell or tissue. The compound can be provided to the first cell either simultaneous with, prior to, or subsequent to providing the first cell the composition of the invention.

The method includes assessing the contractility or the angiogenic activity of the first cell after providing to the first cell both the composition of the invention and the compound, and assessing the contractility or the angiogenic of the second cell, which was not provided the compound, after providing to the second cell the composition of the invention.

A preferred method for evaluating the contractility of a mammalian cell or tissue is described herein in the experimental Examples. Briefly, the contractility of a cell and the effect upon the contractility of a cell can be assessed by determining whether an increase or decrease is observed in the $EC_{50}$ (50% effective concentration) for an inducing compound which mediates contraction of the cell. For example, the $EC_{50}$ can be evaluated for an inducing compound such as PE or AC to determine whether the $EC_{50}$ changes in the first cell after administration of the compound and the composition of the invention. In comparing any change in the $EC_{50}$ observed in the first cell with the $EC_{50}$ for PE in the second cell which is provided the composition of the invention but not the compound, a decrease in the $EC_{50}$ of a cell for PE is an indication of enhanced or disinhibited contractility in the cell, whereas an increase in the $EC_{50}$ of a cell for PE is an indication of inhibited contractility in the cell. Such methods are described herein in the experimental Examples, which describe methods for determining the $EC_{50}$ for an inducing compound such as PE or AC in a muscle cell during contraction.

The method also comprises determining the effect upon the contractility or angiogenic activity of the first cell by comparing the contractility or angiogenic activity of the first cell before providing the composition of the invention with the contractility or angiogenic activity of the first cell after providing both the compound and the composition of the invention. The effect upon the contractility or angiogenic activity of the second cell is also determined by comparing the contractility or angiogenic activity of the second cell before providing the composition of the invention with the contractility or angiogenic activity of the second cell after providing the composition of the invention.

The method thereafter comprises comparing the effect upon contractility or angiogenic activity observed in the first cell with the effect upon contractility or angiogenic activity observed in the second cell. If the effect of the composition of the invention upon contractility or angiogenic activity in the first cell is either increased or decreased by at least about ten percent relative to the effect of the composition of the invention upon contractility or angiogenic activity in the second cell, then a compound is identified which is an agonist or antagonist of one or more of the uPA kringle or a binding protein thereof, the uPA growth factor domain or a binding protein thereof, and the connecting peptide or a binding protein thereof, upon the contractility or angiogenic activity of a mammalian muscle or endothelial cell or tissue.

The invention also includes a method of treating a disease or condition in a mammal having as a symptom thereof one or more of abnormal muscle cell or tissue contractility and abnormal angiogenic activity. The disease or condition can be any of the diseases or conditions described herein. Preferably, the disease or condition is one which has as a symptom thereof abnormal vascular smooth muscle cell or tissue contractility or abnormal bronchial smooth muscle cell or tissue contractility.

The method comprises administering to the mammal an amount suspected to be effective for modulating the contractility and/or angiogenic activity of a mammalian muscle or endothelial cell or tissue of an agonist or antagonist of one or more of the uPA kringle or a binding protein thereof, the uPA growth factor domain or a binding protein thereof, and the connecting peptide or a binding protein thereof. The agonist or antagonist can be administered to the mammal either alone or in the form of a pharmaceutical composition as described herein. The compound can be administered by any route of administration described herein or known to the skilled artisan for administering a compound to a mammal.

Preferably, the agonist or antagonist is administered to the mammal in an amount effective to modulate the effect of one or more of the uPA kringle or a binding protein thereof, the uPA growth factor domain or a binding protein thereof, and the connecting peptide or a binding protein thereof upon the contractility of a muscle tissue in the mammal.

The method comprises providing the agonist or antagonist to a muscle or endothelial cell or tissue in the mammal having abnormal contractility or abnormal angiogenic activity, or to a tissue or fluid of the mammal which is contiguous therewith. The abnormal contractility or angiogenic activity of the muscle or endothelial cell or tissue can be either abnormally high or abnormally low contractility. The agonist or antagonist can be provided to the cell or tissue by any method described herein for providing a compound to a cell directly, such as by contacting the compound with the cell, or indirectly, such as through the action of any biological process. The agonist or antagonist need not be provided to the interior of the cell, since a binding protein of the uPA kringle, a binding protein of the uPA growth factor domain, and a binding protein of the connecting peptide can be found either inside or outside of the cell (i.e. as a soluble protein).

The method also comprises modulating the effect of one or more of the uPA kringle or a binding protein thereof, the uPA growth factor domain or a binding protein thereof, and the connecting peptide or a binding protein thereof, upon the muscle or endothelial cell or tissue having abnormal contractility or abnormal angiogenic activity.

By modulating the effect of one or more of the uPA kringle or a binding protein thereof, the uPA growth factor domain or a binding protein thereof, and the connecting peptide or a binding protein thereof upon the contractility or angiogenic activity of the muscle or endothelial cell or tissue having abnormal contractility or abnormal angiogenic activity, a disease or condition in the mammal having abnormal muscle cell or tissue contractility or abnormal angiogenic activity as a symptom thereof is treated.

By way of example, and not by limitation, in one aspect of the method, the disease or condition treated is the vascular disease hypertension, which has as a symptom thereof abnormally high smooth muscle cell contractility in a vascular smooth muscle cell or tissue. In this embodiment, the mammal is administered an amount suspected to be effective of one or more of an antagonist to the uPA kringle, an antagonist to a binding protein of the uPA kringle, an agonist of the uPA growth factor domain, an agonist of a binding protein of the uPA growth factor domain, an agonist of the connecting peptide, and an agonist of a binding protein of the connecting peptide. In this embodiment, the vascular condition of hypertension in the mammal is treated by inhibiting the contractility enhancing effect of the uPA kringle or one of its binding proteins, or by enhancing the vasodilating effect of the growth factor domain and the connecting peptide and their binding proteins.

In another embodiment of the method, where the disease or condition treated in the mammal is a disease or condition having as a symptom thereof abnormally high bronchial smooth muscle cell or tissue contractility (e.g., asthma), the method comprises administering to the mammal an amount suspected to be effective of one or more of an agonist to the uPA kringle and an agonist to a binding protein of the uPA kringle. In this embodiment, the effect of the uPA kringle in naturally occurring tcuPA at inhibiting bronchial smooth muscle cell contractility (i.e. bronchodilation) is enhanced by the agonist in order to enhance bronchodilation in asthma. Preferably the agonist is administered in an amount effective to promote, increase or amplify the effect of the uPA kringle in naturally occurring tcuPA at inhibiting the contractility of a bronchial smooth muscle tissue, thereby treating asthma in the mammal.

The invention also includes a method of determining whether a test protein is a binding protein of one or more of the uPA kringle, the uPA growth factor domain and the connecting peptide. The method comprises assessing the contractility modulating effect or the angiogenic activity modulating effect of one or more of the uPA kringle, the uPA growth factor receptor and the connecting peptide, in an amount effective to modulate the contractility or angiogenic activity of a mammalian muscle or endothelial cell, upon a first cell or tissue, which either comprises the test protein or which is contiguous with a tissue or fluid of a mammal which comprises the test protein. The test protein need not be present in the first cell or tissue, but can instead be a soluble or circulating protein of a tissue or fluid which is contiguous with the first cell or tissue. For example, the test protein can be a known soluble protein of the bloodstream or lymphatic tissue of a mammal which is capable of direct molecular signaling or signaling indirectly through another molecule to the first cell or tissue.

As with the test protein, the one or more of the uPA kringle, the uPA growth factor receptor and the connecting peptide can either be provided to the first cell or tissue, or to a tissue or fluid which is contiguous with the first cell or tissue, such as a blood or lymph cell or tissue.

The contractility modulating effect or angiogenic activity modulating effect of one or more of the uPA kringle, the uPA growth factor receptor and the connecting peptide, in an amount effective to modulate the contractility or angiogenic activity of a mammalian muscle or endothelial cell, is also assessed in a second, otherwise identical, cell or tissue which does not comprise the test protein and which is not contiguous with a tissue or fluid which comprises the test protein. The one or more of the uPA kringle, the uPA growth factor receptor and the connecting peptide can either be provided to the second cell or tissue, or to a tissue or fluid which is contiguous with the second cell or tissue, such as a blood or lymph cell or tissue.

The contractility modulating effect or the angiogenic activity modulating effect in the first cell or tissue is then compared with the contractility modulating effect or the angiogenic activity modulating effect in the second cell or tissue. If the degree of modulation of contractility or angiogenic activity by one or more of the uPA kringle, the uPA growth factor receptor and the connecting peptide is greater in the first cell or tissue relative to the second cell or tissue, then the test protein is a binding protein of one or more of the uPA kringle, the uPA growth factor receptor and the connecting peptide. The contractility or angiogenic activity of the cells and the contractility modulating effect or angiogenic activity modulating effect of one or more of the uPA kringle, the uPA growth factor receptor and the connecting peptide upon the cells can be assessed using any method known in the art or described herein.

In one embodiment, the contractility modulating effect or the angiogenic activity modulating effect of one or more of an isolated kringle, the ATF, tcuPA, and a peptide or functional element of the uPA kringle is assessed and compared in a first and second cell or tissue. In this embodiment, if a greater increase in contractility or a greater decrease in angiogenic activity is observed in the first cell or tissue relative to the second cell or tissue, then the test protein is a binding protein of one or more of an isolated kringle, the ATF, tcuPA and a peptide or functional element of the uPA kringle.

When present inside the first or second cells, the test protein and/or the one or more of the uPA kringle, the uPA growth factor receptor and the connecting peptide can be present, by way of example and not by limitation, either naturally or as an expressed recombinant polypeptide, or by providing the test protein and/or one or more of the uPA kringle, the uPA growth factor receptor and the connecting peptide to the cells as a component of any of the compositions of the invention described herein using any of the methods described herein for providing a composition or compound to a cell.

The test protein and/or one or more of the uPA kringle, the uPA growth factor receptor and the connecting peptide can also be present in the cells as a naturally occurring protein or as an expressed recombinant polypeptide resulting from the transfection of the cell with any of the vectors described herein comprising a recombinant polynucleotide which encodes the test protein and/or one or more of the uPA kringle, the uPA growth factor receptor and the connecting peptide using any method known in the art or described herein or known in the art to transfect a mammalian cell. The recombinant polynucleotide encoding such a recombinant polypeptide test protein can be prepared by any method known in the art or described herein.

In addition to the method described above, a binding protein of one or more of the uPA kringle, the uPA growth factor receptor and the connecting peptide can be identified using conventional methods known in the art. For example, immunological methods can be used to identify a binding complex of one or more of the uPA kringle, the uPA growth factor receptor and the connecting peptide with a test protein, the specificity of binding and the affinity of the binding complex being an indication that the test protein is a binding protein of one or more of the uPA kringle, the uPA growth factor receptor and the connecting peptide. In addition, the identification of an effect upon any signal transduction event (e.g. calcium release) associated with one or more of the uPA kringle, the uPA growth factor receptor and the connecting peptide can be used to identify a test protein as a binding protein thereof in assays known in the art for assessing signal transduction. Test proteins identified as having an effect upon signal transduction by one or more of the uPA kringle, the uPA growth factor receptor and the connecting peptide are thus identified as binding proteins thereof.

The invention also includes a method of identifying a functional element of one or more of the uPA kringle, the uPA growth factor receptor and the connecting peptide. The functional element participates in the modulation of contractility or angiogenic activity of a mammalian muscle or endothelial cell or tissue. The method comprises preparing one or more mutant polypeptides which lack a portion of the amino acid sequence of one or more of the uPA kringle, the uPA growth factor receptor and the connecting peptide. These mutant polypeptides can be prepared by any method known in the art for preparing deletion mutant proteins or polypeptides. Examples of such methods are described herein in the experimental Examples. The portions of the amino acid sequence which are to be deleted can be determined either randomly or in a directional manner proceeding from either the N-terminal or C-terminal end of the polypeptide and proceeding in a single direction.

The method also comprises assessing the ability of each deletion mutant so prepared to modulate the contractility or to modulate the angiogenic activity of a mammalian muscle or endothelial cell or tissue once provided to the cell or tissue, or to a tissue or fluid which is contiguous with the cell or tissue, as discussed herein. If provided to the cell or tissue; the mutant polypeptide can be provided using any method described herein for providing a composition to a cell or tissue. The modulation of the contractility or angiogenic activity can be either an enhancement, a disinhibition or an inhibition of the contractility or angiogenic activity of any of the muscle or endothelial cell or tissue types described herein. The contraction of the cell can either be mediated or not mediated by any of the inducing compounds described herein. The modulation of contractility or angiogenic activity in a muscle or endothelial cell which is provided a mutant polypeptide can be assessed by any of the methods described herein or known in the art. For example, a decrease or increase in the $EC_{50}$ of an inducing compound during contraction of the muscle cell can be used to assess the ability of the mutant polypeptide to modulate the contractility of the cell or tissue, once provided to the cell or tissue, or to a tissue or fluid which is contiguous therewith.

The method also includes identifying, from the assessment described above, a mutant polypeptide which is not able to modulate the contractility or which is not able to modulate the angiogenic activity of a mammalian muscle or endothelial cell. Based on the identification of a specific mutant polypeptide, the corresponding deleted portion of the amino acid sequence of one or more of the uPA kringle, the uPA growth factor receptor and the connecting peptide which participates in the modulation of contractility or angiogenic activity of a muscle or endothelial cell is determined. Thus, a functional element of one or more of the uPA kringle, the uPA growth factor receptor and the connecting peptide is identified.

In addition to the method discussed above, other methods known in the art for identifying a functional element of a polypeptide can be used. For example, anti-peptide antibodies, deletion/substitution mutants, chimeric polypeptides and other peptide inhibition methods can be used to identify a functional element of one or more of the uPA kringle, the uPA growth factor receptor and the connecting peptide by methods known in the art.

The invention also includes a method of treating a vascular disease or condition in a mammal having as a symptom thereof abnormally high fibrin clot formation. The method comprises administering to the mammal a composition comprising one or more of kringle-scuPA, Δkringle-tcuPA, an antagonist of the uPA kringle and an antagonist of a binding protein of the uPA kringle in an amount effective to inhibit the contractility of a mammalian vascular smooth muscle cell or tissue. The polypeptides Δkringle-scuPA and Δkringle-tcuPA are deletion mutants of the urokinase-type plasminogen activator protein lacking the uPA kringle, which share at least about 75% homology with the polypeptide corresponding to SEQ ID NO:7 (FIG. 1G). Preferably, Δkringle-scuPA and Δkringle-tcuPA are about 80% homologous, more preferably about 85% homologous, even more preferably 90% homologous, yet more preferably 95% homologous, and most preferably about 99% homologous to the polypeptide corresponding to SEQ ID NO:7. Even more preferably, ΔkringlescuPA and Δkringle-tcuPA are each the polypeptide corresponding to SEQ ID NO:7. The antagonist of the uPA kringle and of the uPA kringle binding protein can be any of those described herein.

The method also comprises providing the composition to an affected cell or tissue of the cardiovascular system of the mammal which has or is prone to develop excessive fibrin clot formation, or to a tissue or fluid of the mammal which is contiguous therewith. The composition can be provided using any method described herein for providing to a cell or tissue a composition of the invention. A sufficient period of time is permitted for the uPA protease domain component of the composition, if present, to initiate the breakdown of fibrinogen and the process of fibrin clot lysis and for the composition to cause vasodilation in the affected area by inhibiting the contractility of the vascular smooth muscle cell or tissue in the affected area. Thus, the method results in the promotion of both fibrin clot lysis and vasodilation in the affected area of the vasculature of the mammal, thereby treating the vascular disease or condition.

The method can be used to promote both clot lysis and vasodilation in any vascular tissue in a mammal. The clot can be of any natural origin, such as from any of the diseases or conditions described herein, or of any artificially induced origin, for example, post-traumatic clotting, such as after vascular surgery, stenting or angioplasty. Conventional therapy involves the use of tcuPA to promote clot lysis. However, using tcuPA has the disadvantage of also causing vasoconstriction in the affected area, thus partially defeating the purpose of clot lysis (i.e. to increase blood flow through a vessel). Thus, using Δkringle-tcuPA to promote clot lysis instead of tcuPA has the advantage of overcoming the deleterious vasoconstrictive properties of tcuPA which arise from the contractility enhancing effect of the uPA kringle, while retaining the clot lysis activity of the uPA protease domain. Alternatively, Δkringle-scuPA can be administered to the mammal along with a recombinant version of soluble uPA receptor (suPAR). In this embodiment, the single chain molecule undergoes a conformational change which invests it with clot lysis activity and resistance to its plasma inhibitors. Thus, both Δkringle-scuPA and Δkringle-tcuPA are useful in the inventive method of promoting both fibrin clot lysis and vasodilation in an affected vascular tissue of a mammal.

The invention also includes a kit for treating a disease or condition in a mammal, the disease or condition having as a symptom thereof one or more of abnormal muscle cell or tissue contractility and abnormal angiogenic activity. The kit comprises a composition of the invention in an amount effective to modulate one or more of the contractility and the angiogenic activity of a mammalian muscle or endothelial cell or tissue. The kit also comprises an instructional material which describes administering the composition to a muscle or endothelial cell or tissue of a mammal having abnormal contractility and/or abnormal angiogenic activity.

In another embodiment, this kit comprises a (preferably sterile) solvent suitable for dissolving or suspending the composition of the invention prior to administering the composition to the mammal.

As used herein, an "instructional material" includes a publication, a recording, a diagram, or any other medium of expression which can be used to communicate the usefulness of the composition of the invention in the kit for effecting treatment of the various diseases or conditions recited herein. Optionally, or alternatively, the instructional material may describe one or more methods of treating a disease or condition described herein. The instructional material of the kit of the invention may, for example, be affixed to a container which contains the peptide of the invention or be shipped together with a container which contains the peptide. Alternatively, the instructional material may be shipped separately from the container with the intention that the instructional material and the compound be used cooperatively by the recipient.

The invention is now described with reference to the following Examples. The Examples are provided for the purpose of illustration only and the invention should in no way be construed as being limited to these Examples, but rather should be construed to encompass any and all variations which become evident as a result of the teaching provided herein.

EXAMPLE 1

The objective of the experiments described in this Example was to evaluate the ability of single chain (scuPA) and two chain (tcuPA) urokinase, as well as isolated fragments of urokinase-type plasminogen activator (uPA), to modulate vascular smooth muscle cell (SMC) contractility. Single chain uPA (scuPA) was found to inhibit phenylepherine (PE)-induced contraction of rat aortic rings, whereas two chain uPA (tcuPA) was found to exert the opposite effect. Two independent epitopes mediating these opposing activities were identified. A single chain uPA deletion mutant lacking amino acids 136-143 (the connecting peptide domain) did not induce vasorelaxation. A second epitope within the uPA kringle enhanced PE-induced vasoconstriction. This epitope was exposed when single chain uPA was converted to a two-chain molecule by plasmin. The isolated uPA kringle augmented vasoconstriction whereas the uPA variant lacking the kringle had no procontractile activity. These studies reveal previously undescribed vasoactive domains within urokinase and its naturally-derived fragments. The materials and methods used in the experiments discussed in this Example are described below.

Evaluation of Contractility

Male Sprague Dawley rats (250-275 g) were sacrificed by exsanguination and thoracic aortae were removed with care to avoid damage to the endothelium, dissected free of fat and connective tissue, and cut into transverse rings, each 5 mm in length (Kyong et al., 1992, Br. J. Pharmacol. 107:983-990; Yohtaro et al., 1987, Eur. J. Pharmacol. 131:75-78; Chang et al., 1992, Br. J. Pharmacol. 107:983-990; Oyama et al., 1986, Eur. J. Pharmacol. 132:75-78). The tissues were maintained in an oxygenated (95% $O_2$; 5% $CO_2$) solution of Krebs-Henseliet (KH) buffer (144 millimolar NaCl, 5.9 millimolar KCl, 1.6 millimolar $CaCl_2$, 1.2 millimolar $MgSO_4$, 1.2 millimolar $KH_2PO_4$, 25 millimolar $NaHCO_3$, and 11.1 millimolar D-glucose). The aortic rings were mounted to record isometric tension in a 10 milliliter bath containing KH solution under continuous aeration. The aortic rings were equilibrated for 1.5 hours at 37° C. and maintained under a resting tension of 2 g throughout the experiment. Each aortic ring was then contracted by adding phenylepherine (PE) in stepwise increments raising the concentration of PE from $10^{-10}$ molar to $10^{-5}$ molar. In other experiments, various concentrations of scuPA, tcuPA or uPA fragments were added 15 minutes prior to adding PE. In every experiment, aortic rings exposed to KH buffer alone were analyzed in parallel as controls. Isometric tension was evaluated using a force displacement transducer and recorded online using a computerized system (ExperimentiaAE, Budapest, Hungary).

Conversion of scuPA to tcuPA

In some experiments two chain urokinase (tcuPA; a gift of American Diagnostica, Greenwich Conn.) was studied. tcuPA was documented as free of the isolated amino terminal fragment of uPA on native gels. In other experiments, scuPA or scuPA variants (see below) (20 micromolar each) were incubated with plasmin (0.1 micromolar) for 30 minutes at 37° C. to generate tcuPA. The mixture was added to soluble recombinant human urokinase receptor (suPAR) (see below) bound to CnBr-activated Sepharose (Sigma, St. Louis, Mo.) for one hour at 4° C. (Higazi et al., 1998, Blood 92:2075-2083). The Sepharose beads were washed extensively and the tcuPA was released by adding glycine buffer, pH 3.0. The activity of tcuPA was assessed using the chromogenic substrate S-2444 (Higazi et al., 1996, Thromb. Res. 84:243 -252). The completeness of the conversion of scuPA to tcuPA was verified using sodium docecyl sulfate-polyacrylimade gel electrophoresis (SDS-PAGE) under reducing conditions. The preparation was found to be free of plasmin as judged by cleavage of its chromogenic substrate S-2251 (Chromogenics).

Preparation of Deletion Mutants scuPA$^{\Delta 136-143}$ and $\Delta$kringle-scuPA A plasmid encoding scuPA$^{\Delta 136-143}$ was generated using a two step polymerase chain reaction. The cDNA encoding full length scuPA in pcUK176 served as the template. The primers 5'-CGCGGATCCAGCAATGAAC-3' (SEQ ID NO:19) and 5'-TGGCCACACTGAAATTTTAATTTTC-CATCTGCGCAGTCAT-3' (SEQ ID NO:20) were used to generate the 438 bp 5'-fragment pUN121 (Axelrod, 1989, Molecular and Cellular Biology 9:2133-2141), while 5'-TTAAAATTTCAGTGTGGCCA (SEQ ID NO:21) and 5'-CCAAGCT CGAGGTGCCCG (SEQ ID NO:22) were used to generate the 834 bp 3' fragment. After completion of the second PCR step, the final product was digested using BamHI and XhoI and directionally subcloned into pMT/Bip (Invitrogen, Carlsbad, Calif.) to yield scuPA/$^{\Delta 136-143}$/pMT/Bip. The recombinant protein was expressed using the *Drosophila* Expression System (Invitrogen) in Schneider S2 cells according to the manufacturer's recommendations. scuPA$^{\Delta 136-143}$/pMT/Bip was purified from S2 medium by affinity chromatography using immobilized rabbit polyclonal anti-human uPAR antibody (ImmunoPure Protein G IgG Plus Orientation Kit, Pierce Chemical Co., Rockford, Ill.). scuPA lacking residues 47-135 ($\Delta$kringle-scuPA) was generated by a two step PCR procedure in the same manner. The fragment was digested using Bgl II and Xho I, subcloned into pMT/BiP (Invitrogen) and expressed in Schneider 2 cells. $\Delta$kringle-scuPA was purified from the cell supernatant using SP-Sephadex (Pharmacia, Piscataway, N.J.) and HPLC chromatography. The deletion mutant polypeptide was characterized by SDS-PAGE under reducing and non-reducing conditions followed by Western blot analysis using anti-urokinase antibody.

Purification of uPA kringle

A sample of tcuPA (7.5 mgs/mL) was dialyzed against 0.1 molar sodium phosphate containing 0.6 molar sodium chloride, pH 7.8. Plasmin was added to the dialyzed sample at a final concentration of 1 micromolar and the mixture was incubated at 37° C. for 48 hrs. Pefablock was added at a concentration of 1 micromolar to quench the reaction and the uPA kringle was purified using reverse phase HPLC (RP-HPLC) on a $C_8$ column. N-terminal sequencing analysis of the purified uPA kringle confirmed the N-terminus as starting with Ser$^{47}$ of the mature uPA sequence and the mass of the uPA kringle was determined using Matrix Assisted Laser Desorption Ionisation-Time of Flight (MALDI-TOF) mass spectrometry to be consistent with a composition corresponding to amino acids 47-135 of uPA, having a molecular weight of 10138 Da. The uPA kringle was found to be greater than 95% pure using SDS-PAGE and greater than 99% pure using analytical $C_8$ RP-HPLC.

Preparation of Recombinant Soluble Urokinase Receptor (suPAR)

A cDNA encoding full length uPAR in uPAR/pGEM was used as a template in a PCR reaction to introduce a stop codon after amino acid residue 277 and to introduce restriction enzyme sites (Higazi et al., 1996, Biochemistry 35:6884-6890). The PCR product was subcloned into pMT/Bip at the Bgl II and XhoI sites. The complete sequence was confirmed using automated fluorescence-based sequence analysis. suPAR was expressed using the *Drosophila* Expression System in Schneider S2 cells as described above and purified using affinity chromatography on scuPA-Sepharose (Higazi et al., 1995, J. Biol. Chem. 270:17375-17380).

Assessment of Binding of scuPA$^{\Delta 136-143}$ and $\Delta$kringle-scuPA to the Urokinase Receptor The binding of wild type scuPA, scuPA$^{\Delta 136-143}$, and $\Delta$kringle-scuPA to the urokinase receptor (UPAR) was assessed using a BIA 3000 optical Biosensor (Biacore, AB, Sweden) (Higazi et al., 1996, Biochemistry 35:6884-6890). This method detects binding interactions in real time by measuring changes in the refractive index (RI) at a biospecific surface, enabling the calculation of association and dissociation rate constants. For these studies, suPAR was coupled to a CM5-research grade sensor chip flow cell (Biacore, AB, Sweden) via standard amine coupling procedures using N-hydroxysuccinimide/N-ethyl-N'-[3-(dimethylamino) propyl] carbodiimine hydrochloride (Pierce, Rockford, Ill.) at a level of 500 response units (RU) (Johnsson et al., 1995, J. Mol. Recognit. 8:125-131). The sensor surface was coated using 10 microgram per milliliter solution of suPAR in 10 micromolar sodium acetate buffer, pH 5.0. After immobilization, unreacted groups were blocked with 1 molar ethanolamine, pH 8.5. A second flow cell which was similarly activated and blocked without immobilization of protein served as a control. All binding reactions were performed in phosphate buffered saline, pH 7.4, containing 0.005% TWEEN-20. The binding of scuPA (both wild type and scuPA$^{\Delta 136-143}$) was measured at 25° C. at a flow rate of 60 microliters per minute for 2 minutes, followed by 2 minutes of dissociation. The bulk shift due to changes in RI was measured using the blank surface, and this value was subtracted from the binding signal at each condition to correct for non-specific signals. Binding surfaces were regenerated using two 18 second pulses of 1 molar NaCl, pH 3.5, followed by an injection of binding buffer for 1 min. to remove this high salt solution. All injections were performed in a random fashion using the RANDOM command in the automated method. The binding of urokinase was measured over a range of concentrations from 12.5 nanomolar to 0.2 nanomolar. Data were collected at 2.5 Hz, and fit to a 1:1 Langmuir reaction mechanism using global analysis in the BIA evaluation 3.0 software (Biacore, AB, Sweden). Secondary plots of the data [ln(|dR/dt|) vs time] were also performed to unmask any contribution from mass transport to the kinetic data.

The results of the experiments presented in this Example are now described.

The effect of scuPA and tcuPA upon the phenylepherine (PE) induced contraction of isolated rat aortic rings was studied first. Both of these forms of urokinase contain an identical amino acid sequence, but the molecules differ in their intrinsic enzymatic activity and susceptibility to plasminogen activator (PA) inhibitors. As indicated in FIG. 2, scuPA inhibited PE induced contraction of the aorta, increasing the $EC_{50}$ from 29 nanomolar to 182 nanomolar. scuPA was converted to tcuPA as described in the "Materials and Methods" section above by adding plasmin, which cleaves $Lys^{158}$-$Ile^{159}$, generating a molecule composed of two chains that are linked by a single disulfide bond. The resulting tcuPA was affinity purified using immobilized soluble urokinase receptor (uPAR) or benzamidine to remove plasmin. In direct contrast to scuPA, tcuPA was found to enhance PE-induced aortic contraction, decreasing the $EC_{50}$ of PE from 29 nanomolar to 4.47 nanomolar as shown in FIG. 2.

While not wishing to be bound by any particular theory, it is postulated that single chain and two chain full-length uPA have opposing effects on vascular contractility because they differ in which biologically active epitopes are exposed and/or because the intramolecular interactions among the domains differ. In order to distinguish between these possibilities, experiments were conducted using isolated fragments of urokinase.

Figure 3:
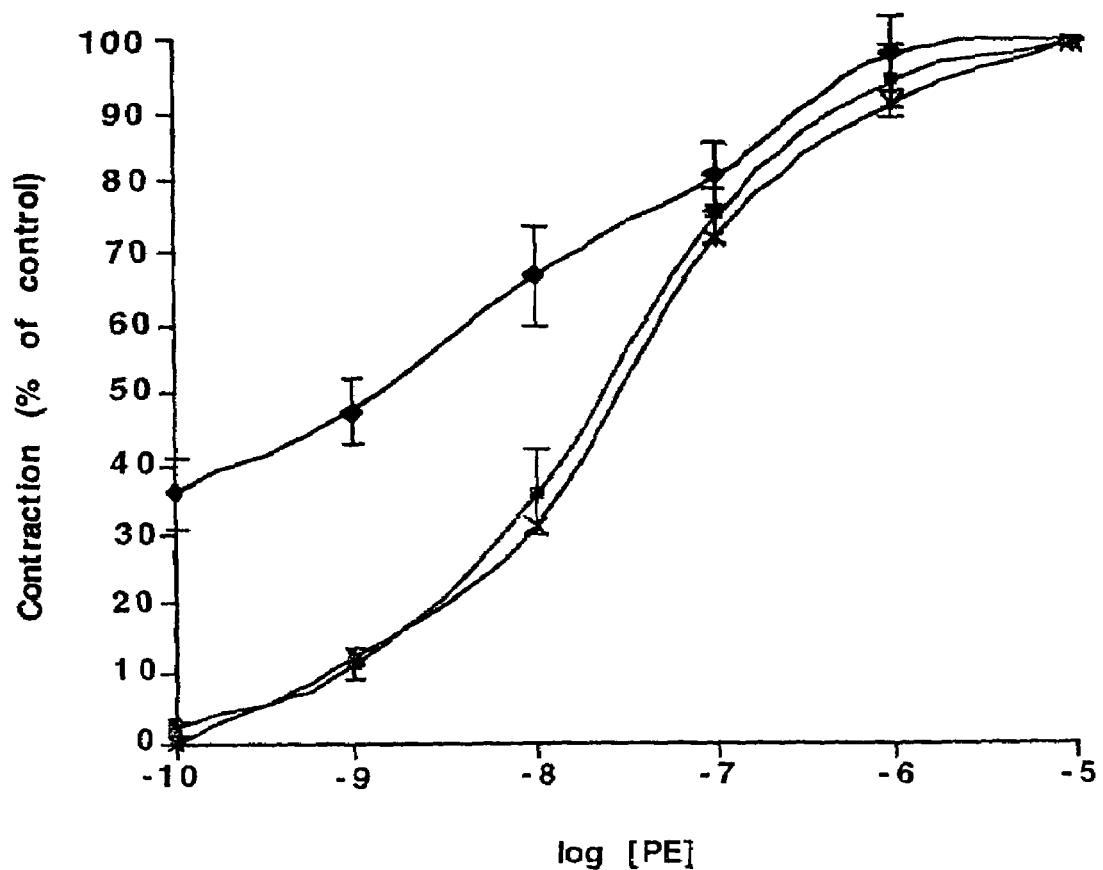
FIG. 3 is a graph depicting the stimulation of PE-induced vasoconstriction by the amino-terminal fragment of uPA (ATF). Aortic rings were contracted by sequential addition of increasing concentrations of PE in K-H buffer (■) or K-H buffer supplemented with 10 nM ATF (♦) or 10 nM ATF+10 nM suPAR (✕). The mean±standard deviation of three experiments is shown.

LMW-uPA, which lacks the amino-terminal fragment and is catalytically active in tcuPA, but nascent in scuPA, exhibited no effect upon PE-induced contraction of aortic rings at concentration as high as 20 micromolar. Therefore, the amino terminal fragment of urokinase (ATF, amino acids 1-135), the portion of the urokinase molecule which binds to uPAR was studied. First, the effect of soluble uPAR (suPAR) upon uPA-mediated vasoconstriction was examined. Binding with suPAR completely abolished the contractility modulating effects of scuPA and tcuPA as evidenced by a return of the $EC_{50}$ to 29 nanomolar. This outcome suggested that uPA-induced aortic contraction was mediated by ATF or a portion of uPA in close enough spatial proximity that it is no longer available when the molecule is bound to its receptor in solution. Isolated ATF was itself found to enhance contractility, as evidenced by the decrease in the $EC_{50}$ for PE to 0.71 nanomolar shown in FIG. 3. Indeed, isolated ATF was found to be 6-fold more potent than tcuPA at enhancing vascular smooth muscle tissue contractility (compare FIGS. 2 and 3) and its activity was abolished by suPAR as well (FIG. 3).

Figure 4:
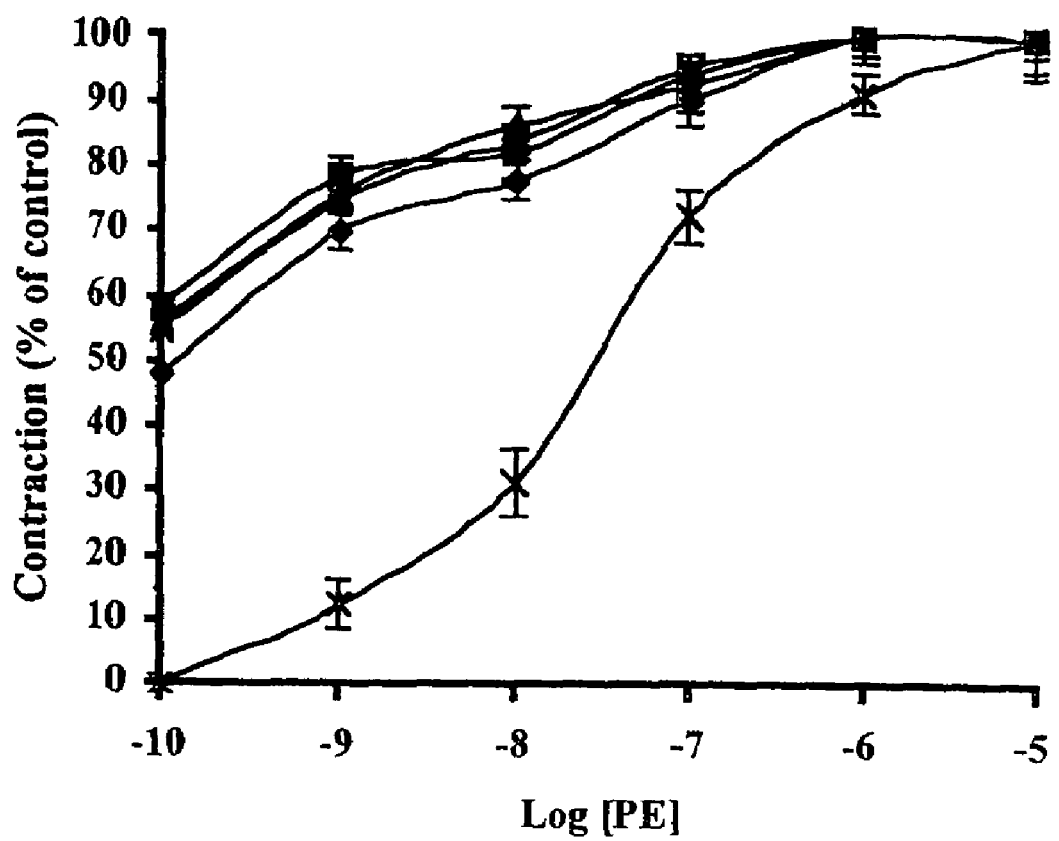
FIG. 4 is a graph depicting the stimulation of PE-induced vasoconstriction by the uPA kringle. Aortic rings were contracted by sequential addition of increasing concentrations of PE in K-H buffer (✕) or K-H buffer supplemented with increasing concentrations of uPA kringle: 1 nM (✱); 10 nM (♦); 50 nM (■); 100 nM (▲). The mean±standard deviation of three experiments is shown.

The aminoterminal fragment of urokinase (ATF) is composed of two subdomains, the growth factor domain (GFD) and the kringle. The GFD is known to mediate the binding of uPA to its receptor. The function of the uPA kringle has heretofore been unknown. In order to determine which portion of ATF was responsible for the contractility enhancing effect of tcuPA and ATF, the effect of each isolated fragment on PE-induced vasoconstriction was assessed. As indicated in FIG. 4, the uPA kringle did not induce vasoconstriction directly, but instead markedly enhanced the effect of phenylepherine. The addition of the uPA kringle at a concentration of 1 nanomolar decreased the $EC_{50}$ from 29 nanomolar to 0.1 nanomolar, whereas GFD added at a concentration of 10 nanomolar did not enhance contractility.

Taken together, these findings indicate that the contractility enhancing effect of tcuPA is mediated by the uPA kringle, an effect which may be overridden in scuPA by a signal involving an adjacent domain termed the "connecting peptide" of urokinase. Alternatively, the pro-contractile epitope of urokinase may be exposed in tcuPA but not in scuPA. To distinguish between these possibilities, a variant of scuPA was prepared which lacked the connecting peptide (scuPA$^{\Delta 136\text{-}143}$), and the vasoactive properties of this variant before and after its conversion to a two-chain molecule were evaluated.

Figure 5A:
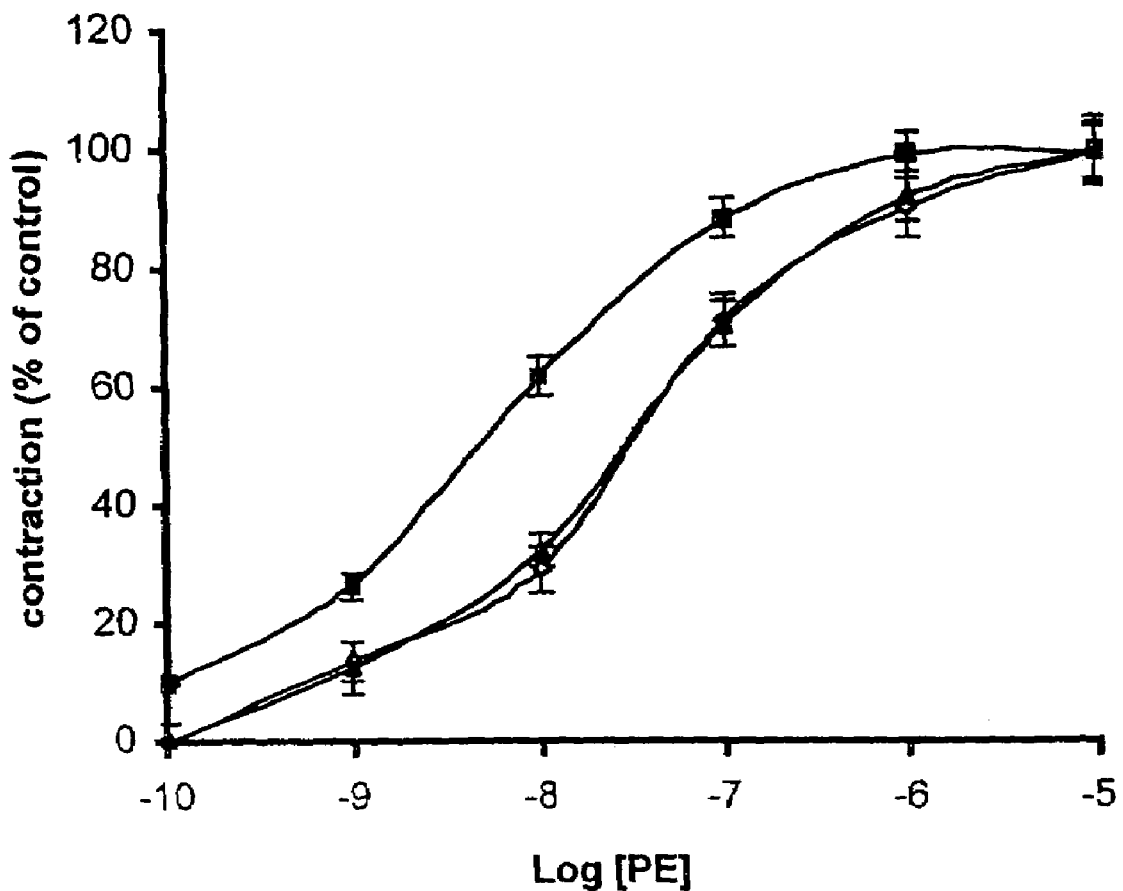
FIGS. 5A and 5B is a pair of graphs depicting the effect of uPA$^{\Delta 136-143}$ and Δkringle-uPA on PE-induced vasoconstriction.

The urokinase variant scuPA$^{\Delta 136\text{-}143}$ was found to exhibit no effect upon PE-induced aortic contraction, as indicated in FIG. 5A. This result demonstrates that the connecting peptide is required to inhibit contraction and that the contractility, enhancing elements in ATF are not active in scuPA. Experiments were then addressed at whether the lack of activity of scuPA$^{\Delta 136\text{-}143}$ was due to a loss of affinity for uPAR. The binding kinetics of wild type scuPA and scuPA$^{\Delta 136\text{-}143}$ to suPAR immobilized on a CM5 sensor chip were measured using a BIA 3000 optical biosensor (see FIG. 6). The binding was found to be kinetically driven, as examination of secondary plots failed to reveal any limitation resulting from mass transport. The variant scuPA$^{\Delta 136\text{-}143}$ bound to suPAR with only a small reduction in Kd compared with wild type scuPA (See Table 1), a difference that cannot account for its complete loss of vascular reactivity. Furthermore, scuPA$^{\Delta 136\text{-}143}$ expressed the same plasminogen activator activity as wild type scuPA in the presence of suPAR and after cleavage by plasmin to a two-chain molecule (Higazi et al., 1995, J. Biol. Chem. 270: 17375-17380; Higazi et al., 1998, Blood 92:2075-2083). In addition, the $EC_{50}$ for PE-induced contraction in the presence of tcuPA$^{\Delta 136\text{-}143}$ and wild type tcuPA were almost identical, as indicated in FIGS. 2 and 5A.

Taken together, this series of experiments suggests that the epitope(s) in the uPA kringle which modulate vascular smooth muscle cell contractility are exposed only when scuPA is converted to tcuPA.

A similar experimental approach was used to determine whether the contractility enhancing effect of tcuPA is due to the overriding influence of the uPA kringle above that of the connecting peptide, in the full urokinase molecule, or whether there was a difference in the exposure of two independently functioning domains. In order to distinguish between these possibilities, the effect of a uPA variant lacking the kringle (Δkringle-uPA) upon PE-induced vasoconstriction was assessed.

The kinetics of binding of wild type scuPA (WT), scuPA$^{\Delta 136\text{-}143}$ and Δkringle-scuPA to immobilized suPAR were measured on the BIA3000 as described in the text. Data from these experiments (sensorgrams shown in FIG. 5) were fit to a 1:1 Langmuir reaction mechanism using global analysis. The equilibrium dissociation constant (Kd) was calculated from the ratio of the kinetic constants (Kd=kd/ka). Table 1 shows the resulting association (ka) and dissociation (kd) rate constants.

TABLE 1

| Analyte | ka ($M^{-1}s^{-1}$) | kd ($s^{-1}$) | Kd (M) |
| --- | --- | --- | --- |
| WT-scuPA | $6.3 \times 10^6$ | $2.1 \times 10^{-3}$ | $3.3 \times 10^{-10}$ |
| ScuPA$^{\Delta 136\text{-}143}$ | $3.3 \times 10^6$ | $3.8 \times 10^{-3}$ | $1.1 \times 10^{-9}$ |
| Δkringle-scuPA | $3.8 \times 10^6$ | $2.2 \times 10^{-3}$ | $0.6 \times 10^{-10}$ |

Figure 5B:
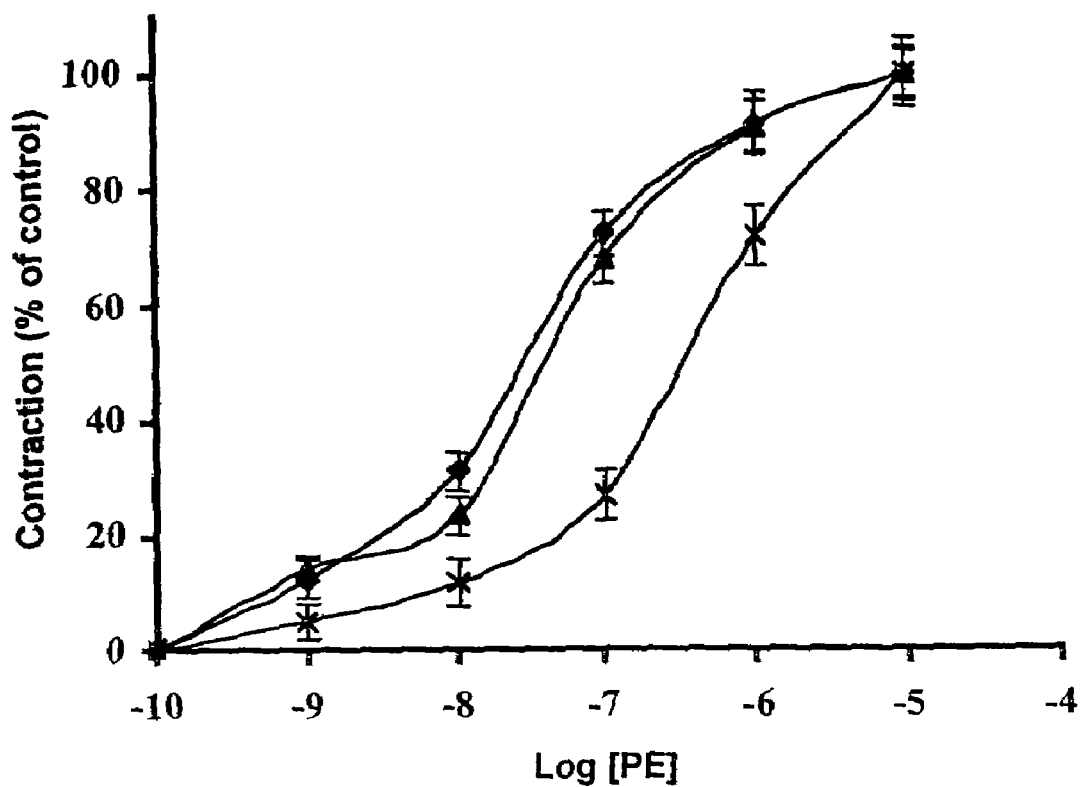
Figure 7:
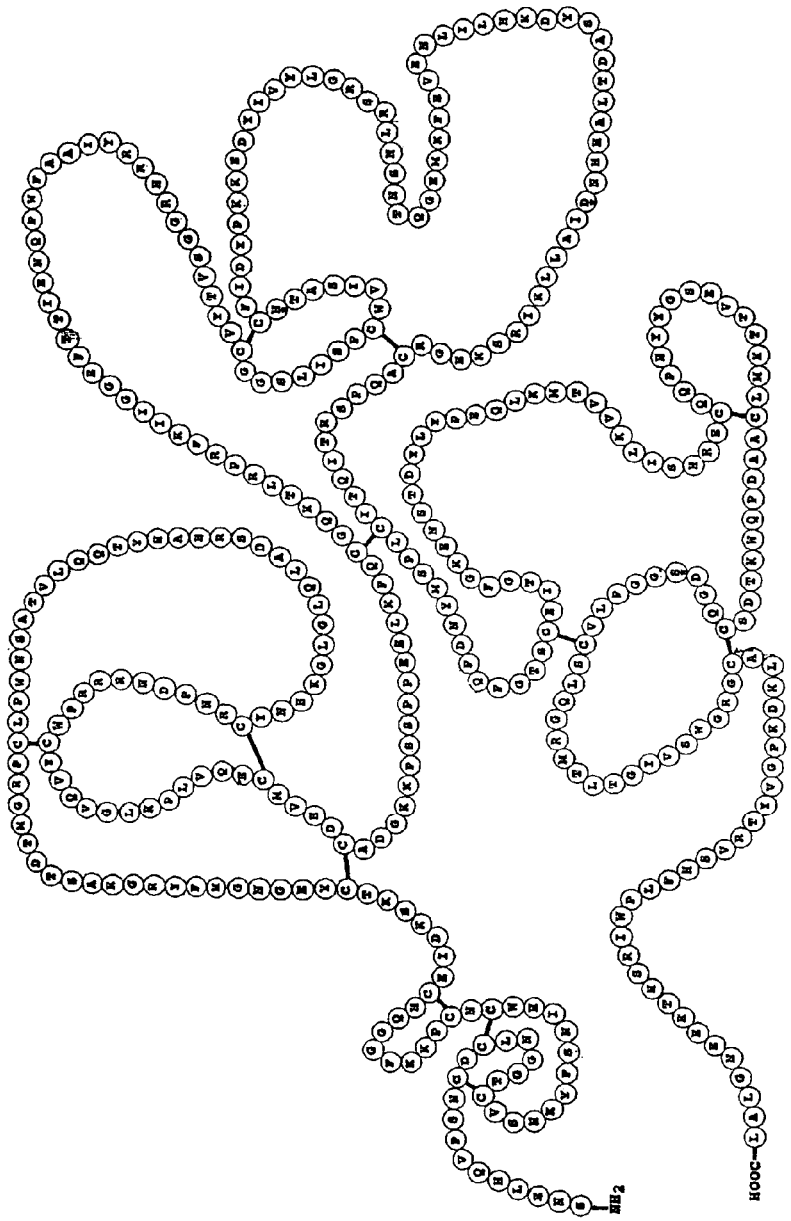
FIG. 7 is a schematic depicting the amino acid sequence (SEQ ID NO:3) of the full uPA protein.

The results of these experiments indicated that Δkringle-scuPA and WT scuPA bound to suPAR with almost the same Kd (Table 1). The variant Δkringle-scuPA also inhibited PE-induced vasoconstriction to the same extent as WT scuPA, as indicated in FIGS. 1 and 5B. However, tcuPA lacking the kringle was unable to enhance PE-induced vascular smooth muscle cell contractility.

SUMMARY

The results of the experiments described above help to reconcile some of the discrepant observations in urokinase-mediated signal transduction by providing novel insights into the nature of intramolecular interactions within the urokinase molecule itself. The finding that single-chain urokinase and two-chain urokinase exert opposing effects upon smooth muscle cell contractility provides not only the first described effect of this plasminogen activator upon contractility, but also provides compelling evidence for the existence of more than one functionally active site within the molecule.

One epitope, located within the connecting peptide (amino acids 136-143), inhibits vasoconstriction induced by phenylepherine and endothelin by blocking the release of calcium from intracellular stores as well as its entry from the extracellular space. The effect of the connecting peptide upon vasorelaxation is sequence specific and requires both $Ser^{138}$ and $E^{143}$. Further support for the concept that the connecting peptide functions as a biologically active unit derives from its capacity to inhibit cell migration and tumor cell invasiveness.

A second epitope, within the uPA kringle, enhances PE induced vasoconstriction. This contractility enhancing epitope and the epitope within the connecting peptide which inhibits contractility are not exposed simultaneously in either single-chain or two-chain uPA. Only the connecting peptide is exposed in scuPA. This conclusion is established by several findings. First, a variant of scuPA lacking only these eight amino acids neither causes vasorelaxation nor vasoconstriction. On the other hand, the epitope within the uPA kringle is exposed only in tcuPA. This conclusion is based on two observations: deleting the uPA kringle did not inhibit the effect of scuPA on vasorelaxation, but the deletion abolished its contractility enhancing activity as a two-chain molecule. Second, plasmin-mediated activation of scuPA exposes a contractility enhancing epitope within the amino terminal fragment co-incident with the loss of the inhibitory epitope within the connecting peptide. This conclusion derives from the observation that cleavage of the scuPA variant lacking the connecting peptide by plasmin generates a two chain variant molecule possessing the same pro-contractile potency as wild type tcuPA but does not inhibit PE-induced vasoconstriction as a single chain molecule.

Thus, the results of the experiments described above provide evidence that a polypeptide comprising one or more domains of uPA, selected from the uPA kringle, the growth factor domain and the connecting peptide, is effective at modulating the contractility of a mammalian muscle cell or tissue, and can be used advantageously as part of a composition to be administered to a mammal for the treatment of a disease or condition having as a symptom thereof abnormal muscle cell or tissue contractility.

EXAMPLE 2

Figure 8:
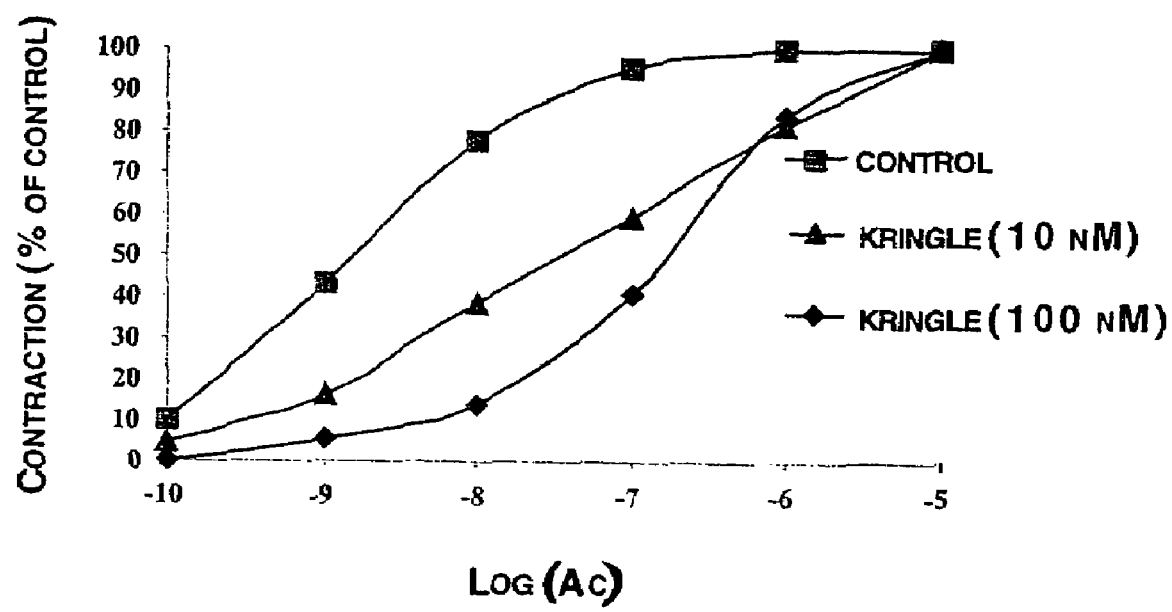
FIG. 8 is a graph depicting the effect of the uPA kringle upon the AC-induced contraction of isolated rat tracheal rings. Isolated rat tracheal rings were either pre-incubated with media containing 10 nanomolar or 100 nanomolar uPA kringle or with control media lacking the uPA kringle, and then with varying concentrations of acetylcholine (AC). The tension in the rings upon AC-induced contraction was measured and is shown as a percent of the contraction of the control. The mean±standard deviation of three independent experiments is shown.

The objective of the experiments described in this Example was to evaluate the ability of the uPA kringle to modulate bronchial smooth muscle cell or tissue contractility. The effect of the uPA kringle upon acetylcholine induced contraction of isolated rat tracheal rings was evaluated. Isolated rat tracheal rings were either pre-incubated with media containing 10 nanomolar or 100 nanomolar uPA kringle or with control media lacking the uPA kringle. Varying concentrations of acetylcholine (AC) were then added as an inducing compound to induce contraction and the tension in the rings upon AC-induced contraction was measured. FIG. 8 depicts the results of these experiments, with contractility being shown as a percent of the contraction of the control. The mean±standard deviation of three independent experiments is shown.

The results of these experiments indicate that the uPA kringle inhibits the contractility of rat tracheal tissue in a dose-dependent manner, as indicated by the increase in $EC_{50}$ for acetylcholine-induced contraction shown in FIG. 8 for tracheal rings pre-treated with either 10 nanomolar or 100 nanomolar uPA kringle. Thus, compositions comprising the uPA kringle can be used to treat respiratory diseases and conditions having as a symptom thereof abnormally high bronchial smooth muscle cell or tissue contractility, such as asthma, adult respiratory distress syndrome, primary pulmonary hypertension and chronic intrapulmonary fibrosis.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating a mammal afflicted with asthma having as a symptom thereof abnormal muscle cell or tissue contractility, said method comprising a) administering to the mammal a pharmaceutical composition comprising the amino acid sequence consisting of SEQ ID NO:9 in an amount effective to modulate the contractility of a mammalian muscle or endothelial cell or tissue and a pharmaceutically acceptable carrier; and b) modulating the contractility of said muscle or endothelial cell or tissue having abnormal contractility, whereby said asthma in the mammal is treated.

* * * * *